(12) United States Patent
Moodley

(10) Patent No.: US 8,033,083 B2
(45) Date of Patent: Oct. 11, 2011

(54) PROCESS AND MACHINE FOR AUTOMATED MANUFACTURE OF GASTRO-RETENTIVE DEVICES

(75) Inventor: Jagathesan Moodley, Athlone (IE)

(73) Assignee: Merrion Research III Limited (IE)

( * ) Notice: Subject to any disclaimer, the term of this patent is extended or adjusted under 35 U.S.C. 154(b) by 0 days.

(21) Appl. No.: 12/687,976

(22) Filed: Jan. 15, 2010

(65) Prior Publication Data

US 2010/0115751 A1 May 13, 2010

Related U.S. Application Data

(63) Continuation of application No. 11/572,838, filed as application No. PCT/EP2005/00831 on Aug. 1, 2005, now Pat. No. 7,669,388.

(60) Provisional application No. 60/592,454, filed on Jul. 30, 2004.

(51) Int. Cl.
B65B 7/00 (2006.01)
(52) U.S. Cl. ............. 53/468; 53/454; 53/492; 53/266.1; 53/381.1
(58) Field of Classification Search .................... 53/449, 53/457, 468, 492, 284, 381.1, 381.4, 900, 53/454, 266.1
See application file for complete search history.

(56) References Cited

U.S. PATENT DOCUMENTS 3,552,095 A * 1/1971 Inman .............................. 53/390
3,786,813 A 1/1974 Michaels
3,944,064 A 3/1976 Bashaw et al.

(Continued)

FOREIGN PATENT DOCUMENTS

CA 2214923 3/1999

(Continued)

OTHER PUBLICATIONS

Notification of Transmittal of the International Search Report and the Written Opinion of the International Searching Authority, or the Declaration corresponding to International Application No. PCT/IB2004/003414 mailed May 31, 2005.

(Continued)

*Primary Examiner* — Paul Durand
(74) *Attorney, Agent, or Firm* — Myers Bigel Sibley & Sajovec, PA

(57) ABSTRACT

An improved automated process and apparatus for making a gastro-retentive device (10). The method includes the steps of providing a pouch assembly (18) having an ingredient section within a membrane; rotating the membrane to form a folded pouch assembly; inserting the folded pouch assembly into a first capsule section (20*a*) to form a pouch/first capsule assembly, and inserting the pouch/first capsule assembly into a second capsule section (20*b*). The process can further include the steps of providing a continuous strip (32) of multiple pouch assemblies (18) and cutting a single pouch assembly (18) from the strip (32). Also provided is an apparatus (100) for carrying out the above method which includes three wheels (102, 104, 106) for processing and moving the capsule sections (20*a*, 20*b*), a pouch load subassembly (166) for delivering a strip (32) of pouch assemblies (18) to a pouch load tooling mechanism (168), a pouch wrapping subassembly which, after receiving the pouches (18) from the pouch load tooling mechanism (168) wraps the flaps of the pouches which are then, via a pouch insert subassembly 200, inserted into the first capsule section (20*a*) in one of the wheels (104). The second capsule section (20*b*) is then combined with the first capsule section (20*a*) in the wheel (104) to complete the finished gastro-retentive device (10).

6 Claims, 18 Drawing Sheets

U.S. PATENT DOCUMENTS

| | | | |
|---|---|---|---|
| 4,055,178 A | | 10/1977 | Harrigan |
| 4,207,890 A | | 6/1980 | Mamajek et al. |
| 4,285,987 A | | 8/1981 | Ayer et al. |
| 4,595,583 A | | 6/1986 | Eckenhoff et al. |
| 4,731,979 A | * | 3/1988 | Yamamoto et al. ............. 53/529 |
| 4,773,907 A | | 9/1988 | Urquhart et al. |
| 4,782,644 A | * | 11/1988 | Haarer et al. ................... 53/282 |
| 4,996,058 A | | 2/1991 | Sinnreich |
| 5,081,822 A | * | 1/1992 | Boyd et al. ...................... 53/468 |
| 5,198,229 A | | 3/1993 | Wong et al. |
| 5,417,030 A | * | 5/1995 | Ribani et al. .................... 53/281 |
| 5,474,092 A | * | 12/1995 | Moser et al. .................. 131/280 |
| 5,817,335 A | | 10/1998 | Wong et al. |
| 5,966,910 A | | 10/1999 | Ribani et al. |
| 6,120,801 A | | 9/2000 | Parekh et al. |
| 6,120,803 A | | 9/2000 | Wong et al. |
| 6,170,226 B1 | * | 1/2001 | Chang ................................ 53/64 |
| 6,245,350 B1 | | 6/2001 | Amey et al. |
| 6,290,989 B1 | | 9/2001 | Asmussen et al. |
| 6,367,228 B1 | * | 4/2002 | Wurst et al. .................. 53/381.4 |
| 6,656,501 B1 | | 12/2003 | Cooker |
| 7,082,738 B2 | * | 8/2006 | Konishi et al. .................. 53/281 |
| 2006/0191239 A1 | | 8/2006 | Moodley |

FOREIGN PATENT DOCUMENTS

| | | |
|---|---|---|
| DE | 1174244 B | 7/1964 |
| DE | 3314894 A1 | 1/1984 |
| EP | 0376711 A1 | 4/1990 |
| EP | 0376711 A1 | 7/1990 |

OTHER PUBLICATIONS

Notification Concerning Transmittal of International Preliminary Report on Patentability (Chapter I of the Patent Cooperation Treaty) corresponding to International Application No. PCT/IB2004/003414 mailed Feb. 16, 2006.

Notification of Transmittal of the International Search Report and the Written Opinion of the International Searching Authority, or the Declaration corresponding to European Patent Application No. EP2005/008310 mailed Mar. 6, 2006.

Notification Concerning Transmittal of International Preliminary Report on Patentability (Chapter I of the Patent Cooperation Treaty) corresponding to European Patent Application No. EP2005/008310 mailed Feb. 23, 2007.

* cited by examiner

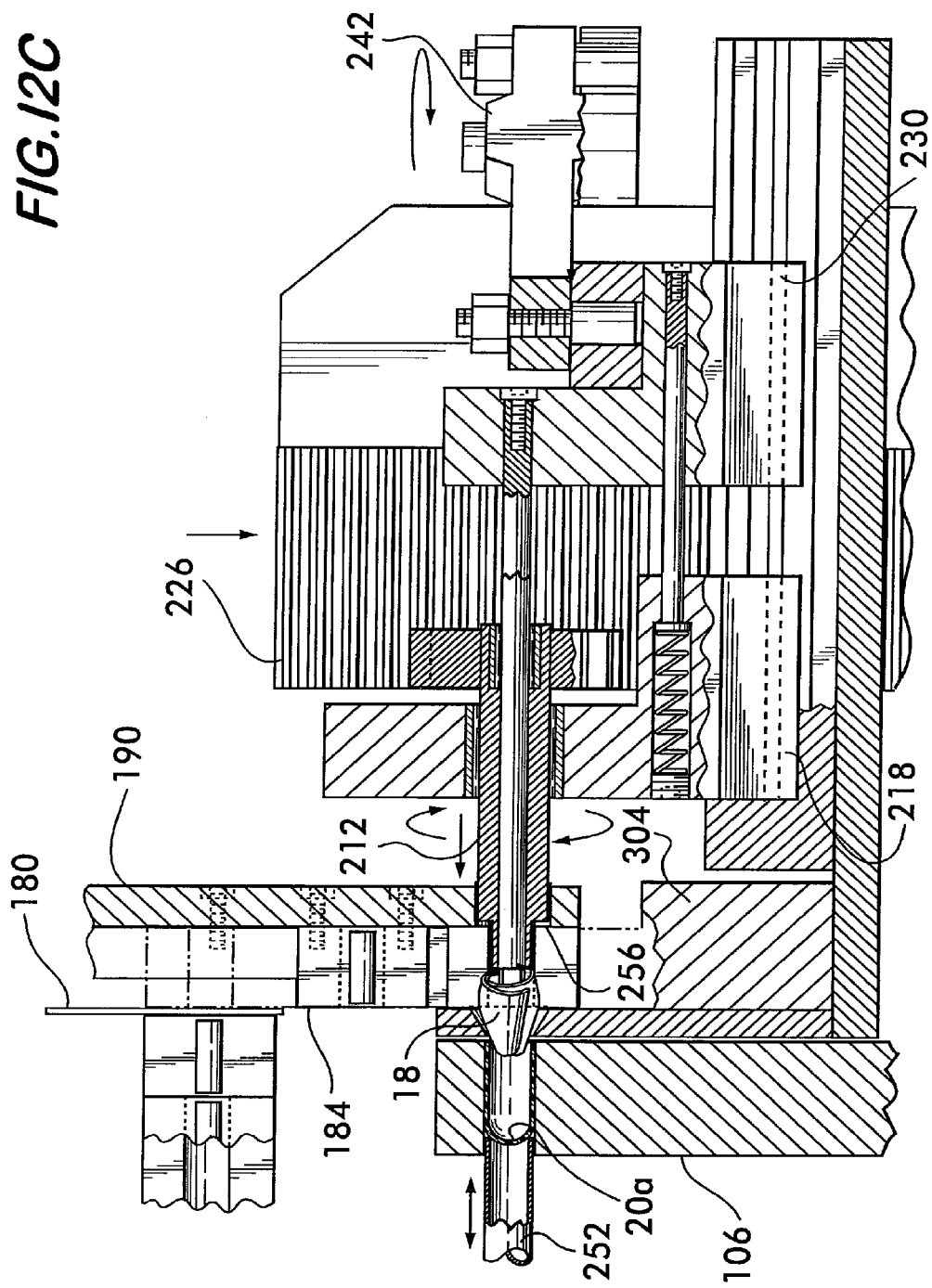

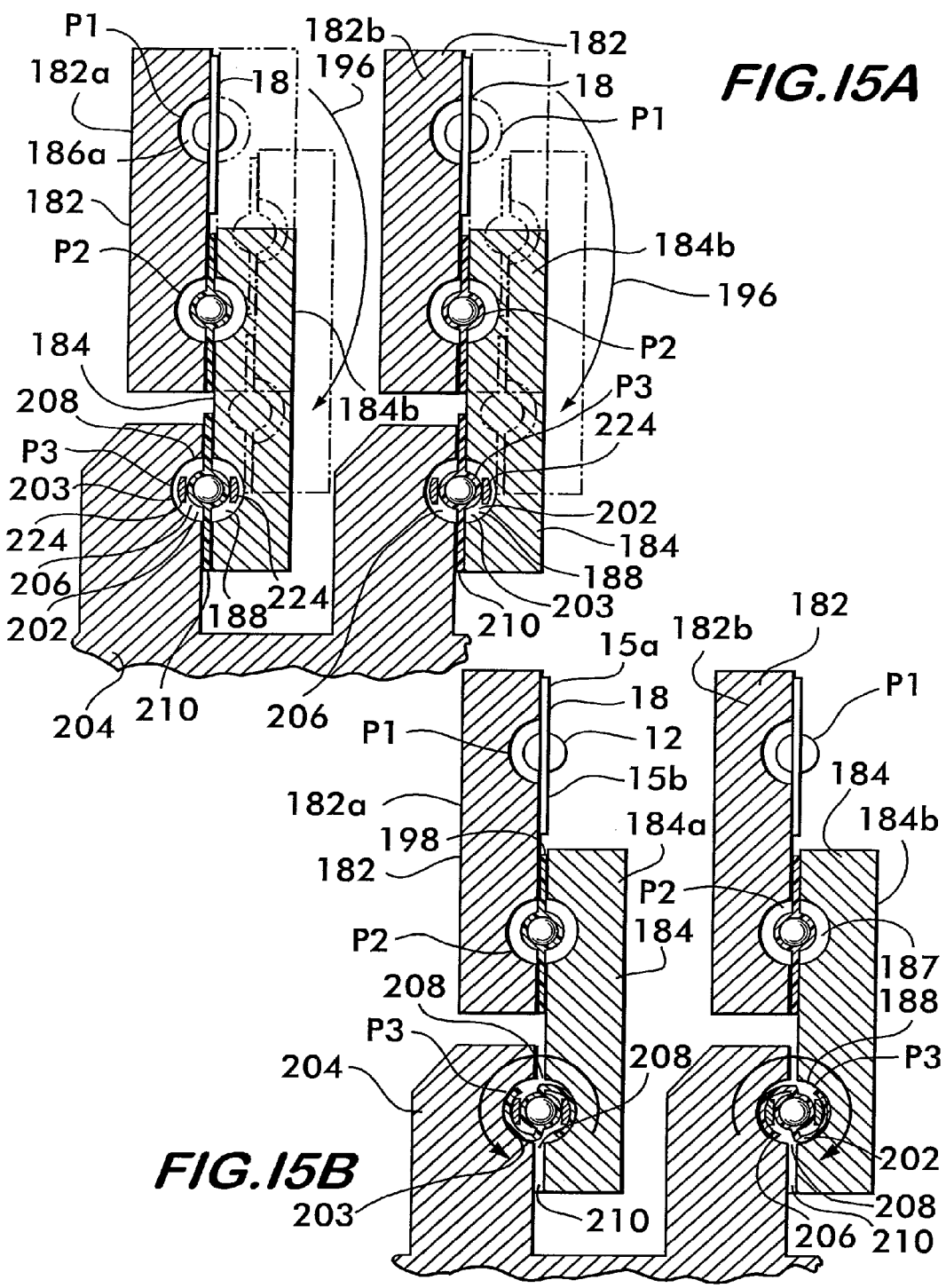

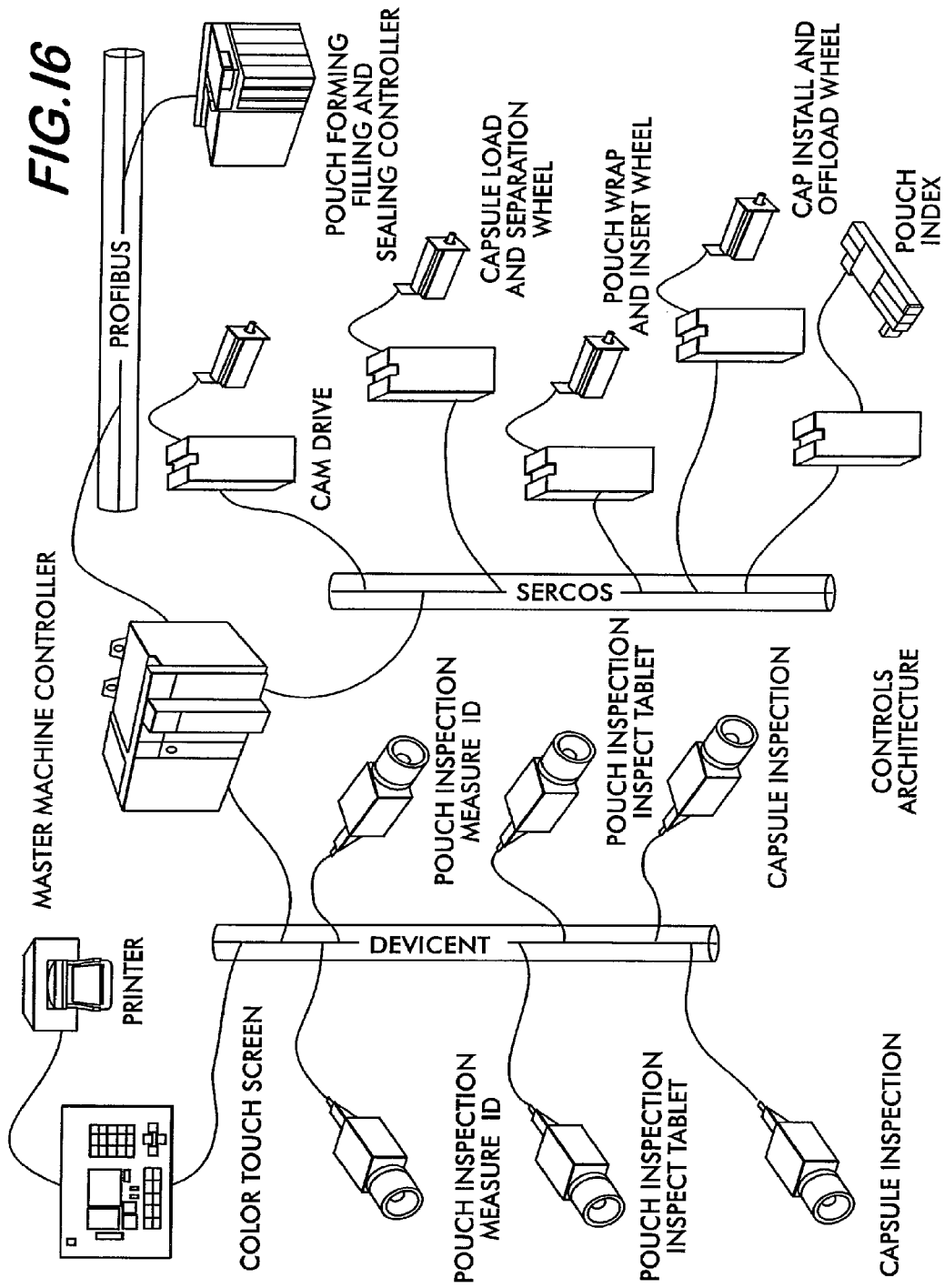

PROCESS AND MACHINE FOR AUTOMATED MANUFACTURE OF GASTRO-RETENTIVE DEVICES

CROSS-REFERENCE TO RELATED APPLICATION

This application is a continuation of U.S. application Ser. No. 11/572,838 filed on Jan. 29, 2007, now U.S. Pat. No. 7,669,388 which is a 35 U.S.C. §371 national phase application of PCT Application No. EP2005/00831 filed on Aug. 1, 2005 which claims the priority of U.S. Provisional Application No. 60/592,454 filed Jul. 30, 2004, the disclosure of which are hereby incorporated herein by reference in their entireties.

BACKGROUND

The present invention relates to a process and an apparatus for the automated manufacture of a gastro-retentive device. An example of such a device is a retard form of the type disclosed in U.S. Pat. No. 4,996,058, which is hereby incorporated herein by reference, although the present invention is not limited to such retard forms and is applicable to any gastro-retentive device.

The term "retard form," denotes a dosage form which effects delayed release of at least a portion of the active ingredient in the stomach and to the upper part of the small intestine in comparison to conventional dosage forms, such as customary tablets or capsules. Avoiding an undesirably high initial dose, the release is effected continuously over a relatively long period and controlled at an effective level. The retard form is administered orally and, once in contact with the stomach fluids, expands so as to float on the stomach fluids and/or be retained within the space of the stomach due to its size following inflation, which precludes passage across the pylorus sphincter. In this manner it remains in the stomach to insure continuous controlled release of the physiologically active ingredients.

A retard form is characterized preferably, at least in one form, by the following: (a) at least one component that expands on contact with bodily fluid (e.g., a substance that generates or constitutes a blowing agent), and/or a physiologically active substance, and/or a combination of physiologically active substances, and/or optionally a pharmaceutically acceptable hydrophilic swelling agent and further pharmaceutically acceptable adjuncts, (b) at least one hydrophilic membrane which surrounds component (a) and which is expansible at the site of use and is permeable to body fluid, and (c) a covering which surrounds component (a) and membrane (b) and which disintegrates without delay under the action of bodily fluid at the site of use in the stomach, e.g., a gelatin capsule.

As an example, a retard form of this type suitable for the present invention could take the following form. A component (a) is provided in the form of a tablet surrounded by and sealed within component (b) in the form of a hydrophilic membrane or film, the membrane forming a pouch in which the tablet sits. The tablet and membrane assembly are fitted within component (c) provided in the form of a gelatin capsule.

Taken orally, the retard form moves to the stomach where the gelatin capsule disintegrates to release the tablet membrane assembly. Upon contact with stomach fluid, the tablet generates the blowing agent, for example carbon dioxide gas. The gas causes the membrane surrounding the tablet to inflate, forming a gas-filled "bag." This gas-filled "bag" is able to float on the stomach fluids and/or is unable to pass through the pylorus sphincter following inflation, and thus is retained in the stomach. During its dwell time in the stomach, any active ingredients present in the tablet are released slowly and/or in a controlled manner into the surrounding body fluid, preferably by diffusion, through the membrane. Since gastric juice is being transported further into the upper part of the small intestine, the active ingredient passes continuously and over a prolonged period into the duodenum and jejunum, where it can be absorbed over an extended period. The retard form ensures continuous release of any active ingredient in conjunction with uniform absorption, or at least that the device will remain in the stomach for the desired time period. Once the gas generating components are used up, and/or the when the "bag" deflates to a certain size, the remainder of the device can pass through the body.

The manufacture of a gastro-retentive device of the general type described above can be complex and includes several challenges. The component(s) (a) or tablet must be sealed within the membrane(s) to form the pouch. Depending on the drug or drugs of choice, the tablet may also contain other excipients which control the release of the drug or drugs from the tablet into the medium of the pouch and subsequently into the gastric fluid of the stomach following diffusion across the pouch. Once formed, the pouch must be folded to fit within the capsule. While such gastro-retentive devices can be produced manually, it is believed that an automated and economical process for producing such forms will help bring the benefits of gastro-retentive devices to the public.

SUMMARY OF THE INVENTION

The present invention provides a method and apparatus for the automated manufacture of a dosage form that requires folding or wrapping for insertion into a capsule. One such dosage form, by example, is a gastro-retentive device that preferably has at least the following components: 1) an ingredient section which includes a physiologically active substance or substances and optionally a gas generating substance, 2) a film or membrane surrounding the ingredient section so as to form a pouch that has at least one flap, the combination of the ingredients and the pouch being referred to as a pouch assembly, and 3) a capsule surrounding the pouch assembly and which is capable of disintegrating upon contact with bodily fluids to release the pouch assembly, the capsule having first and second cap sections. The method includes the steps of providing a continuous strip of pouch assemblies, separating a single pouch assembly from the strip; wrapping the flap of the pouch assembly, inserting the folded pouch assembly into the first cap section; and inserting the first cap/pouch assembly into the second cap section to complete an encapsulation of the pouch assembly. Other dosage forms are believed possible to which the present invention will apply. An apparatus for carrying out the above method is also provided.

BRIEF DESCRIPTION OF THE DRAWINGS

The following detailed description will be better understood when read in conjunction with the figures appended hereto. For the purpose of illustrating the invention, there is shown in the drawings a preferred embodiment. It is understood, however, that this invention is not limited to this embodiment or the precise arrangements shown.

FIG. 3A is an enlarged view of the area shown in circle 3A of FIG. 3;

FIG. 12C is a cross sectional view taken along line 12-12 of FIG. 9 showing the push rod pushing the wrapped pouch into the capsule body;

FIG. 15A is a view taken along line 15A,B-15A,B of FIG. 9 before the pouch is wrapped;

FIG. 15B is a view taken along line 15A,B-15A,B of FIG. 9 after the pouch is wrapped; and FIG. 16 is a schematic view of a control and vision system for the present invention.

DETAILED DESCRIPTION OF THE INVENTION

The present invention provides a novel method for making a gastro-retentive device. The method of the present invention permits automation of the manufacturing process and allows the economical and reliable manufacture of such forms.

An apparatus for carrying out the method of the present invention is also provided.

An exemplary gastro-retentive device 10 to be manufactured in accordance with the present invention is illustrated with reference to FIGS. 1, 1A and 1B. FIG. 1B shows the completed encapsulated device 10 which is now described in further detail.

Figure 1:
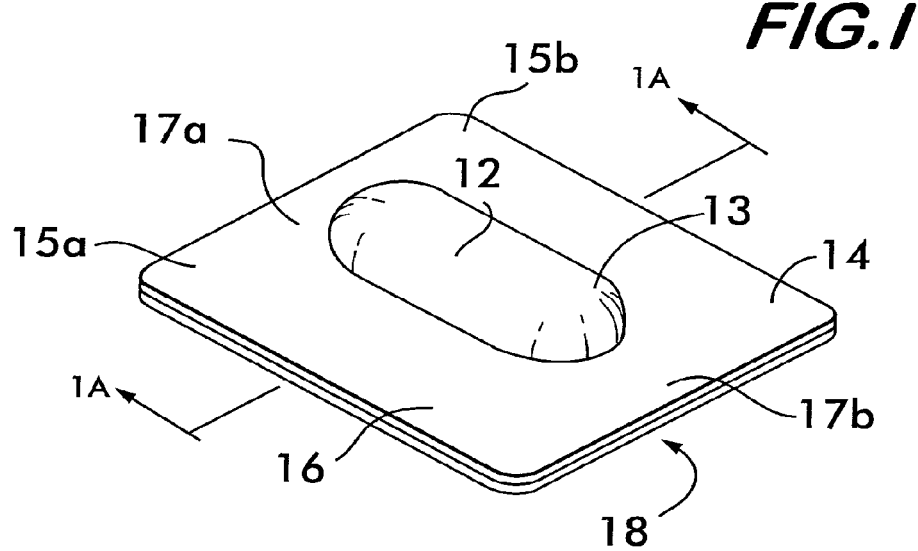
FIG. 1 is a perspective view of an ingredient/pouch assembly for an exemplary gastro-retentive device.
Figure 1A:
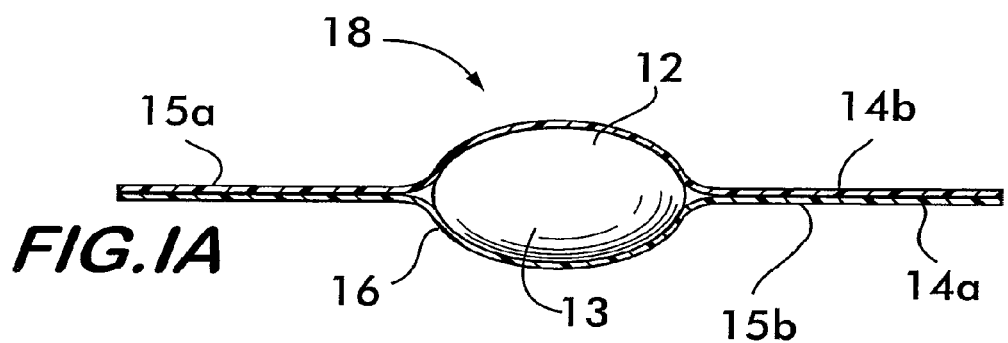
FIG. 1A is a cross sectional view taken along line 1A-1A in FIG. 1.
Figure 1B:
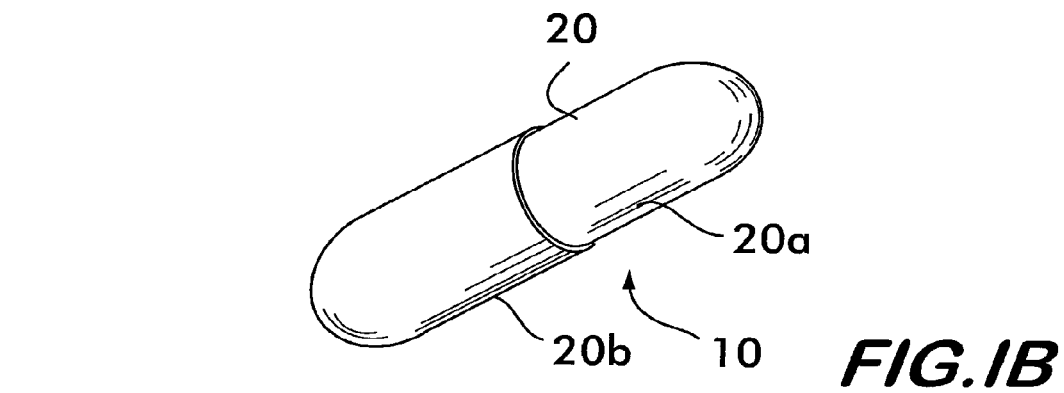
FIG. 1B is a perspective view of the encapsulated gastro-retentive device with the ingredient/pouch assembly of FIG. 1 inside the capsule.

With particular reference to FIGS. 1 and 1A, the gastro-retentive device contains the desired ingredients, which combination of, for example, can include any one of physiologically active ingredients, excipients, and blowing agents, collectively the "active ingredients". An example of the active ingredients is component (a), as discussed above in the background section, at least a portion of which is preferably provided in a centralized or common ingredient section 12, and which is preferably provided in the form of a tablet 13. The tablet 13 is preferably formed in a flattened capsule shape such as a deep or normal concave caplet shape; having dimensions of about 3 mm height and maximum length and width of about 16 mm long by 6 mm wide. Nominal tablet weight is 640-750 mg, and tablet hardness approximately 50 Newtons. Other shapes, sizes and configurations may be suitable depending on the desired use. While a solid tablet 13 is used for illustration purposes herein, it is understood that other forms of the ingredient section 12 may be used and that the present invention is not to be limited to solid tablets.

Surrounding the folded ingredient section 12 is a film or membrane 14 (an example being component (b) as described in the background section), configured to form a pouch 16 which is inflatable upon the generation of gas from the ingredient section 12 within to form a gas-filled "bag." The membrane is preferably provided in two layers, a bottom layer 14a and top layer 14b, with the ingredient section 12 sandwiched in between. The two membrane layers 14a, 14b are heat sealed together to form the sealed pouch 16. The areas of the pouch surrounding the ingredient section 12 are referred to as flaps 15a, 15b. (There may also be front and back flaps 17a, 17b). The flaps include any evacuated portion of the pouch 16 extending from the ingredient section 12. The membrane film preferred is a polyvinylaclcohol (PVA) having a thickness of approximately 150 μm (±10 μm), and which is typically formed of two membrane layers sealed together. The pouch 16 is preferably between about 20 mm×20 mm and 25 mm×25 mm inside dimensions although other sizes may be suitable depending on the desired use. The seal width is preferably about 2 mm to 3 mm in addition to the inside dimensions indicated all around the pouch. The combination of the ingredient section 12 and pouch 16 will be referred to herein as the ingredient/pouch assembly 18, or pouch assembly 18, as shown in FIGS. 1 and 1A. The corners of the pouch assembly 18 are rounded as shown to help prevent damage during processing.

Surrounding the ingredient/pouch assembly 18 is a capsule 20 (component c as discussed in the background section) having a first capsule section 20a (the capsule body), and a second capsule section 20b (the capsule cap). See FIG. 1B. The capsule 20 disintegrates quickly when exposed to the stomach fluids to release the pouch assembly 18. The capsule is preferably gelatin, having a size range suitable to contain the ingredient section 12 and pouch, sizes 0EL and 00EL being preferred for the illustrated embodiment. The pouch assembly 18 is fitted inside the capsule in a folded, compact form. As discussed below, the flaps 15a, 15b are preferably folded or wrapped around the ingredient section 12 of the pouch assembly 18 to fit within the capsule 20. Once the capsule disintegrates, the pouch assembly 18 contacts the bodily fluids and inflates to form the "bag" as described previously.

Figure 2:
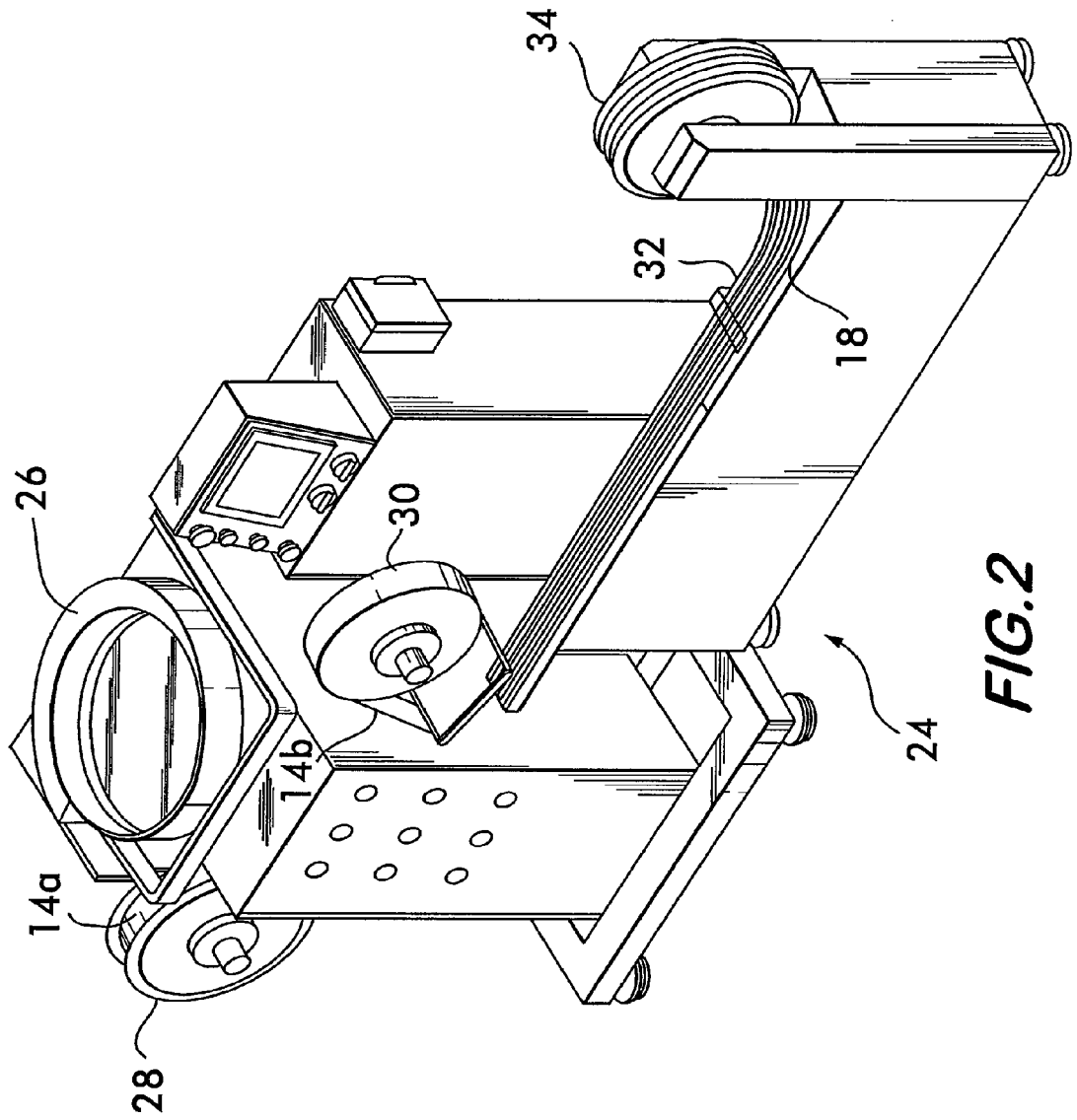
FIG. 2 is a perspective view of a pouch packaging machine.

One method of making the retard form 10 of the present invention begins with the manufacture of the pouch assembly 18. Shown in FIG. 2 is a pouch packaging machine 24 for producing a strip 32 of attached ingredient/pouch assemblies, each of the assemblies 18 being of the type illustrated in FIGS. 1 and 1A and which use a tablet 13 for the ingredient section 12. A tablet hopper 26 receives and holds the tablets 13 which are produced through methods known in the art. A first spool 28 of film 14 is provided for forming the first or lower membrane layer 14a, and a second spool 30 of film 14 is provided for forming the second or upper membrane layer 14b. The spools are automatically maintained at the proper tension.

A tablet 13 is controllably released from the hopper 26 onto the lower membrane layer 14a in the desired orientation. The upper membrane layer 14b is then laid on top of the tablet 13. (With films that have a backing, the backing is rewound for removal and disposal). The machine 24 automatically punches a hole in at least one of the films 14a, 14b through which air can be evacuated during a subsequent sealing process. Alternatives are possible. With the tablet sandwiched between the two films 14a, 14b, the films are pressed together and the air between the two layers evacuated through the punched hole to a desired vacuum level.

The two films are then sealed together with a heating element pressed into contact with the film to produce a seal around the tablet 13, preferably air tight, of about 2 to 3 mm in width (the air evacuation hole being on the outside of the seal), thereby forming the sealed tablet/pouch assembly 18. The sealing temperature is preferably between 200-210° C. with a dwell time of about two seconds. The machine 24 can produce multiple tablet/pouch assemblies 18 during each cycle, the completed tablet/pouch assemblies forming a continuous strip 32 of tablet/pouch assemblies 18 which can be rolled up into a spool 34, or fed directly to a tablet pouch fold encapsulation machine for further processing as described below. The machine 24 can be controlled by a programmable controller as is known in the art. Other evacuation and sealing methods are contemplated. For example, three of the four sides of the films/tablet assembly could be heat sealed first, then the air evacuated from the pressed films/tablet assembly on the unsealed side, followed by sealing the last side. Moreover, the tablet can be inserted into the pouch after the three sides are sealed, the fourth side then being sealed after the tablet is inserted and the air evacuated by vacuum.

Other means of making the tablet/pouch assembly 18 are known. For example, a customized machine from Prodo-Pak Corporation of Garfield, N.J., USA, model number RV 925 WS-4 pouch forming and sealing machine, can be used.

A preferred embodiment of a pouch wrap and encapsulation machine 100 is now described with reference to FIGS. 3 to 16. The encapsulation machine 100 receives the pouch assembly 18 and, through the automated steps described below, produces an encapsulated gastro-retentive device 10 as shown in FIG. 1B. The machine 100 of the present embodiment can process more than one pouch assembly 18 and capsule 20 at a time in each process step, here two at a time, although it will be understood that the machine 100 can process a single pouch assembly 18 and capsule 20 in each step if desired.

Figure 3:
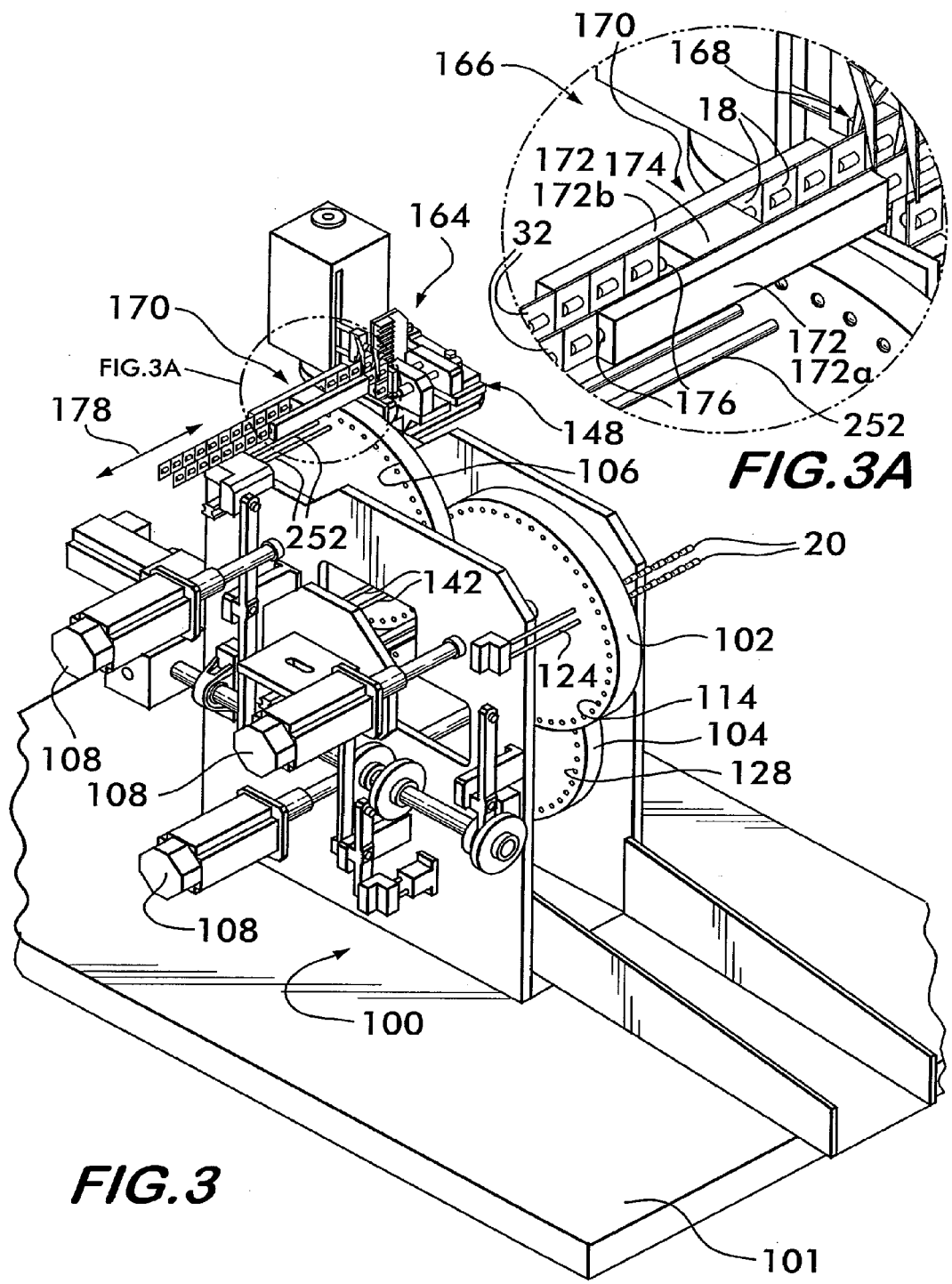
FIG. 3 is a perspective view of an encapsulation machine of the present invention.
Figure 4:
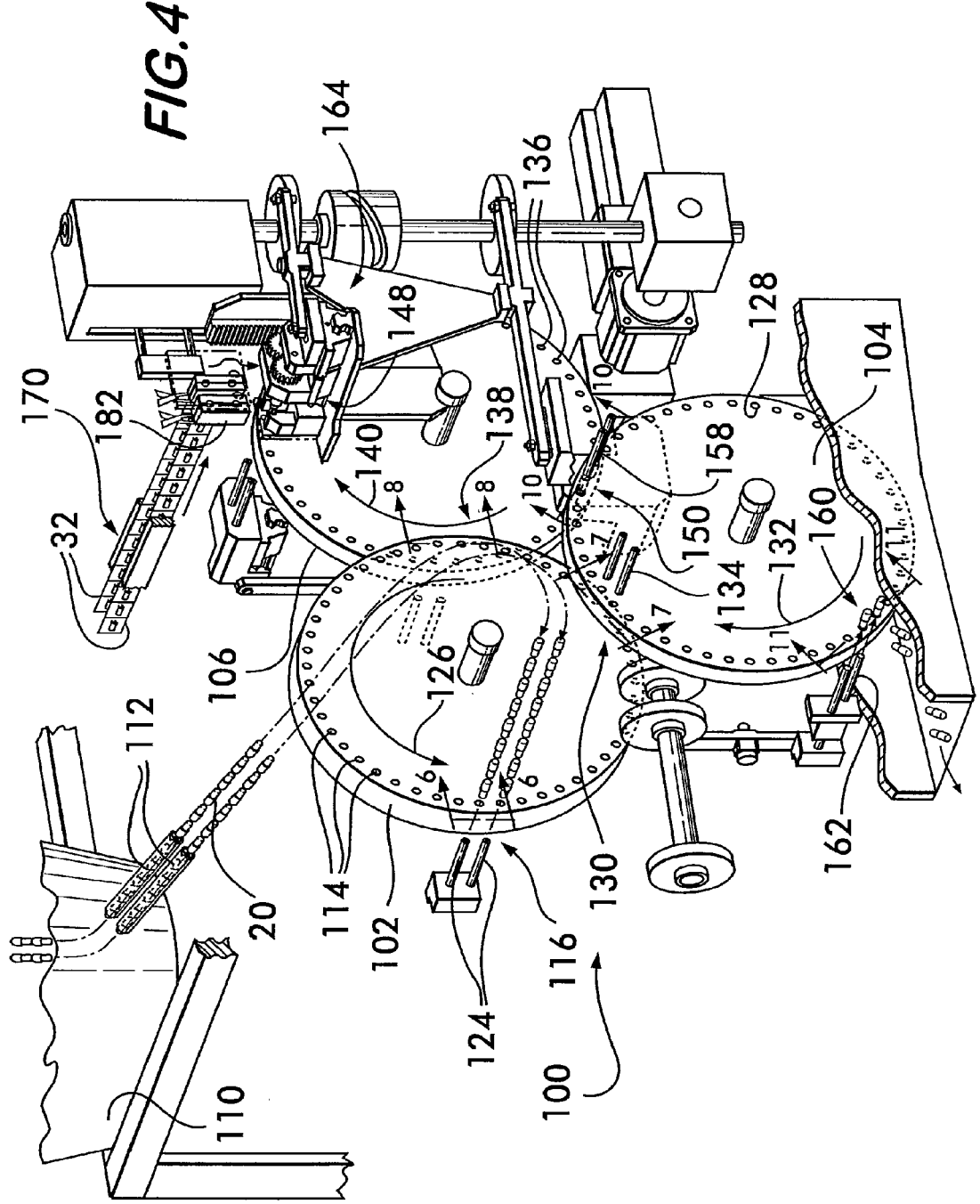
FIG. 4 is a perspective view of the encapsulation machine of FIG. 3 shown from another angle.

With reference to FIGS. 3 and 4, the present machine 100, shown mounted on a support table 101, has three capsule assembly wheels 102, 104, and 106 arranged as shown. Each of the wheels are mounted so as to be rotatable in the directions of the arrows (126, 132, 140) as shown (FIG. 4) for radial indexed motion. Servo-motors 108 connected to each wheel by a shaft provide the radial indexed motion. As further discussed below, the wheels have cylindrical openings 114, 128, 136 extending through the wheels for retaining and moving the capsules 20 during the encapsulation process. As an overview of the encapsulation process, the wheels 102, 104, 106 are used in the various steps to receive and separate the capsules 20 into the capsule body 20a and capsule cap 20b sections. The capsule body and cap are received by wheel 102. The capsule cap 20b is then transferred from wheel 102 to wheel 104, and the capsule body 20a is transferred from wheel 102 to wheel 106 which delivers the capsule bodies 20a to a pouch processing section 164 where the pouches are loaded into the machine, wrapped, and inserted into the capsule bodies 20a. The wheel 106 then delivers the capsule bodies 20a containing the folded pouch assemblies 18 to the capsule caps 20b in wheel 104 for completing the encapsulation process. The process steps, and machine 100 for carrying out these steps, are now described in more detail.

The empty gelatin capsules 20, each having a first capsule section (capsule body) 20a and second capsule section (capsule cap) 20b, are fed to the machine 100 by a capsule feeder 110 supported above the machine 100 (shown partially in FIG. 4). The capsule feeder 110 delivers capsules 20 oriented end to end through two feed tubes 112 to openings 114 in the first wheel 102. Such gel capsule feeders are known in the art. In one such feeder, as known in the art, feeder 110 has a bowl which feeds the capsules to two orienting rolls to orient the capsules diameter-to-diameter hanging with the larger diameter (cap) up. A venturi system can be provided to draw the oriented capsules 20 through the tubes 112. Two feed tubes 112 are provided as the present embodiment processes two capsules and pouches in each process step. The tubes 112 are positioned to discharge the capsules 20 directly into the openings 114 at a particular wheel index position 116 where a discharge end of the tubes 112 align with the wheel openings 114. The capsules 20 are provided in an unlocked form, i.e., the capsule cap 20b is not locked to the capsule body 20a.

Figure 6:
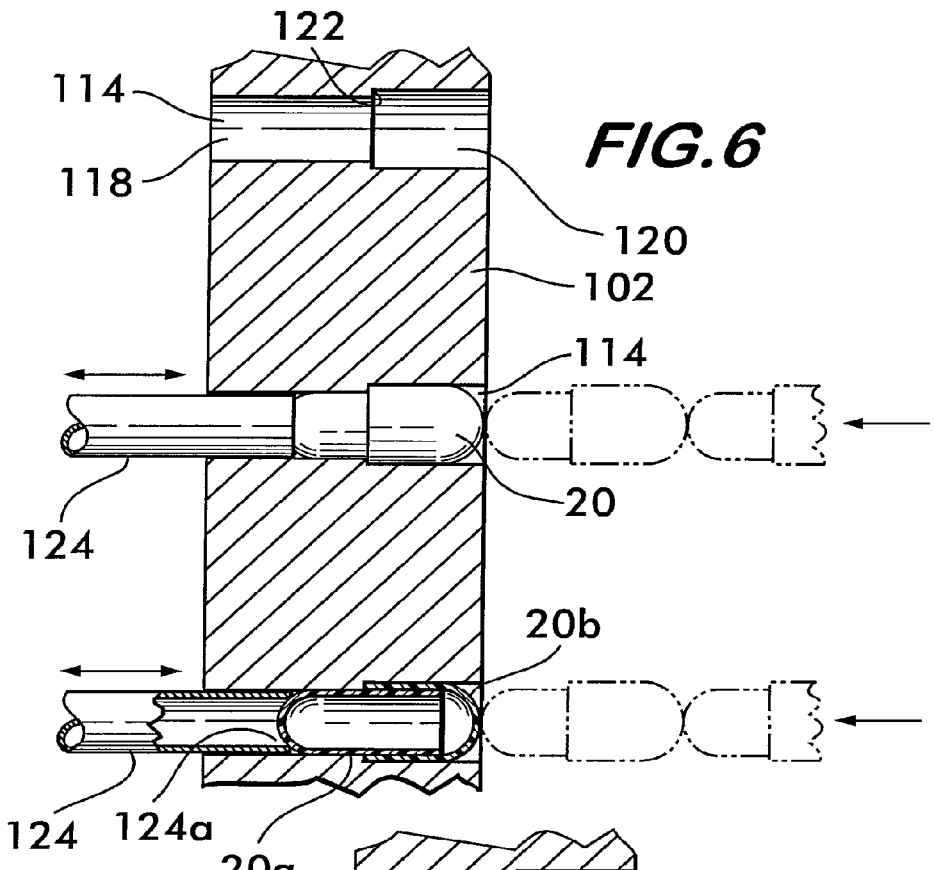
FIG. 6 is a view taken along line 6-6 of FIG. 4.

The first wheel 102, referred to herein as the capsule load and separation wheel, is preferably approximately 12 inches in diameter with 48 evenly spaced cylindrical openings 114 near the wheel perimeter. With further reference to FIGS. 4 and 6, each wheel opening 114 is sized to receive a capsule 20, having a first section 118 of suitable width/diameter for receiving the capsule body 20a, and which is smaller than the width/diameter of the capsule cap 20b, and a second section 120 having a width/diameter larger than that of the first section 118 for receiving the larger capsule cap 20b. A shoulder 122, formed by the change in diameter from the first to the second sections 118, 120 acts to limit the movement of the capsule 20 within the opening 114. As illustrated in FIG. 6 the capsules 20 are inserted into the openings 114 on the side of the wheel 102 having the wider section 120 until the capsule bodies 20b contact the shoulders 122. The wheel openings 114 receive the two capsules 20 from the two tubes 112 at about the same time.

For further processing, the capsule sections 20a and 20b are separated within the openings 114. A pair of hollow vacuum rods 124, each having a concave end matching the shape of the end of the capsule bodies 20a, and having a vacuum port 124a for gripping the capsule body, are moved into the opening 114 to grip the capsule bodies 20a and move them leftwardly to the opposite end of the openings 114 as oriented in FIG. 6. The shoulder 122 prevents movement of the capsule cap 20b as the capsule body 20a is moved to the left as illustrated in FIG. 6. A vacuum generation device, not shown, generates the necessary vacuum in a manner known in the art. Two additional wheel openings 114 receive a new set of capsules 20 for processing after each indexed movement of the wheel 102 in the direction of the arrow 126 (FIG. 4).

Figure 7:
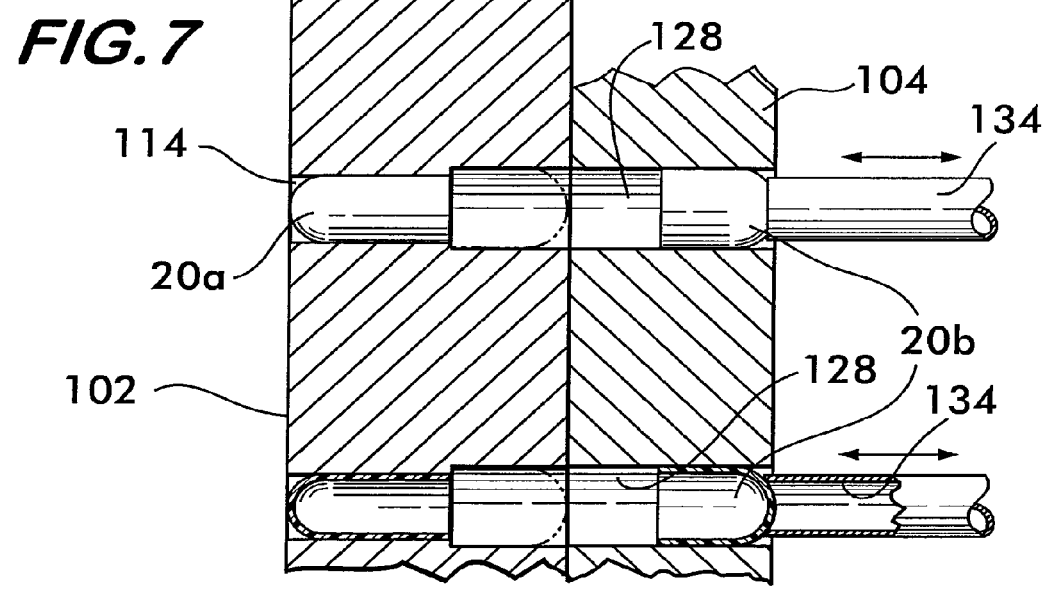
FIG. 7 is a view taken along line 7-7 of FIG. 4.

With reference to FIGS. 4 and 7, the second wheel 104, referred to as the capsule cap install and offload wheel, receives the capsule caps 20b from the first wheel 102 (the capsule load and separation wheel). The wheel 104 is preferably approximately 12 inches in diameter with 48 evenly spaced openings 128 near the wheel perimeter. Each wheel opening 128 is sized to receive a capsule cap 20b. Two openings 114 of the first wheel 102 and two openings 128 of the second wheel 104 align at an axial index position 130 where the two wheels 102, 104 overlap one another (FIG. 4). As each wheel 102, 104 is radially indexed in the direction of the respective arrows 126, 132, two new sets of openings 114 and 128 come into alignment with one another after which capsule caps 20b are transferred from the wheel 102 to the wheel 104 by a pair of vacuum rods 134 that move in and out of the openings 128 in a similar manner as described above with respect to vacuum rods 124.

Figure 5:
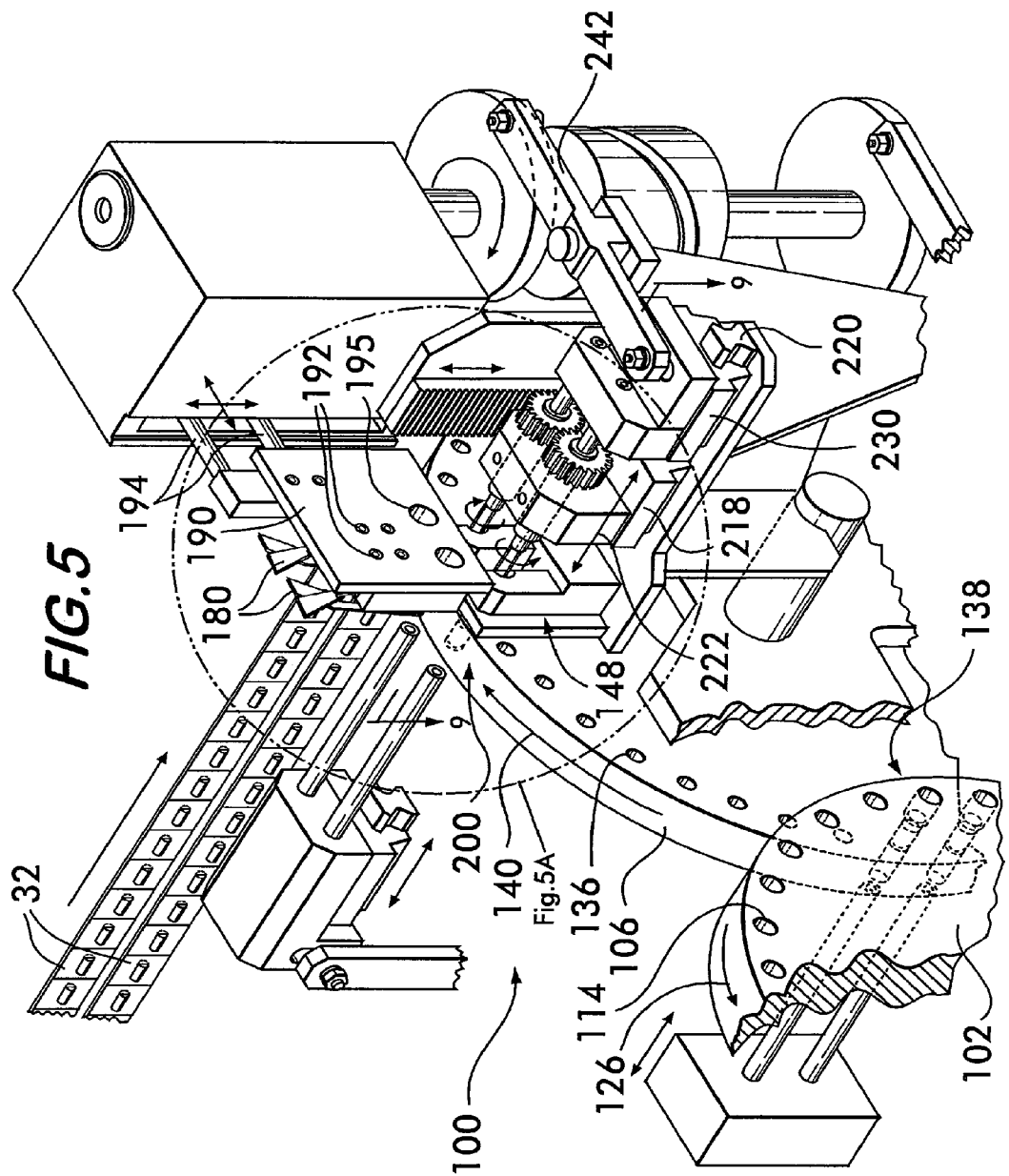
FIG. 5 is an enlarged view of the pouch wrapping area shown in FIG. 4 of the encapsulation machine.
Figure 8:
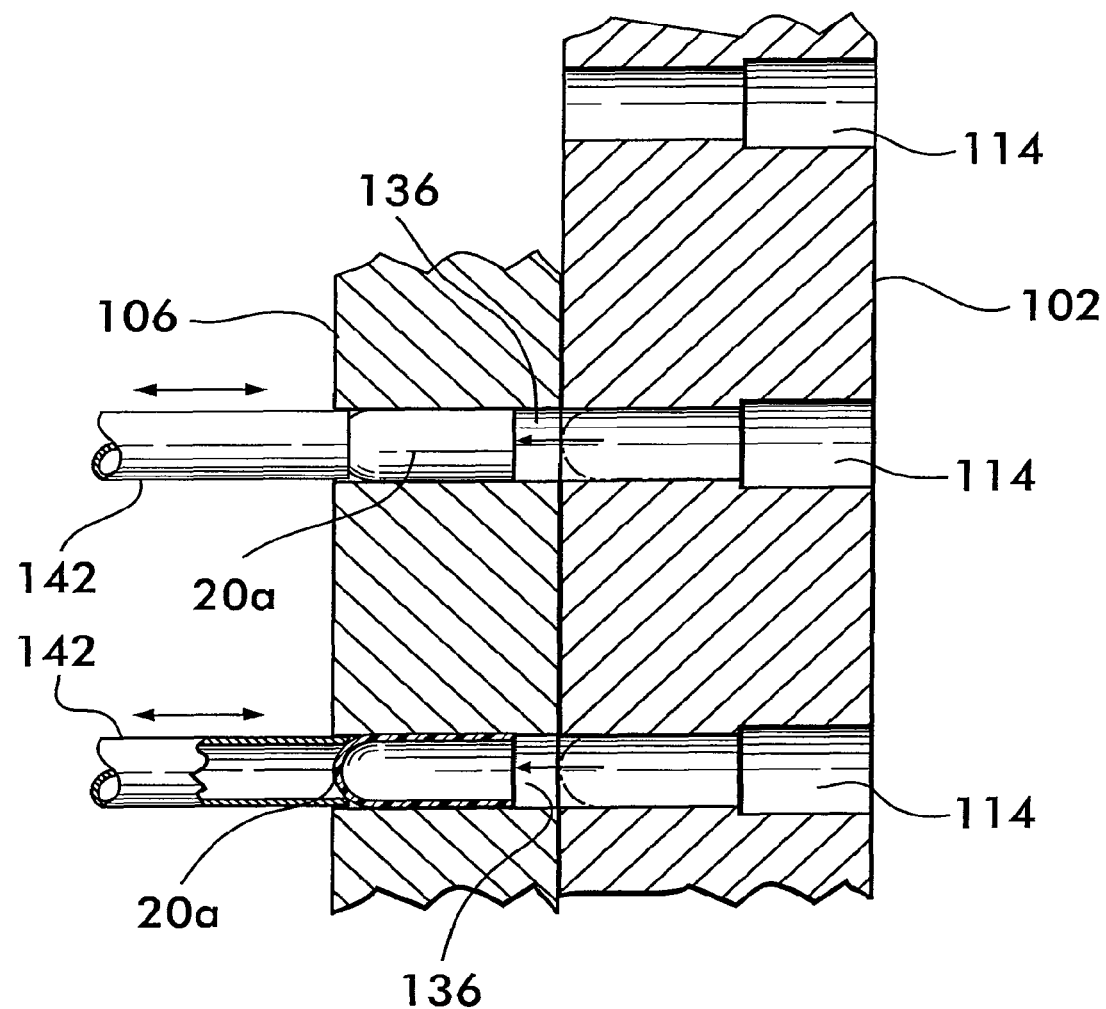
FIG. 8 is a view taken along line 8-8 of FIG. 4.

The third wheel 106, referred to herein as the pouch wrap and insert wheel, receives the capsule bodies 20a from the first wheel 102 (the capsule load and separation wheel). The wheel 106 shown is preferably 12 inches in diameter with 48 evenly spaced openings 136 near the wheel perimeter. As illustrated in FIGS. 4, 5 and 8, two openings 114 of the first wheel 102 and two openings 136 of the third wheel 106 align at an axial indexed position 138 where the two wheels 102, 106 overlap one another after each wheel is radially indexed in the direction of respective arrows 126, 140. The capsule bodies 20a are transferred from the wheel 102 to the wheel 106 by a pair of hollow vacuum rods 142 that move in and out of the openings 136 in a manner similar to that described above with respect to vacuum rods 124. As is further discussed below, the wheel 106, upon further indexing in the direction of arrow 140, delivers the capsule bodies 20a to the pouch processing section 164 where the pouches are wrapped and inserted into the capsule bodies 20a. After the wrapping process, the wheel 106, after further indexing in the direction of arrow 140, delivers the capsule body/pouch assemblies 144 to the second wheel 104 where the capsule bodies are combined with the capsule caps 20b as described below in more detail.

As noted above, the second wheel 104, in addition to receiving the capsule caps 20b from the wheel 102, also receives the capsule bodies 20a from the wheel 106 after the pouch assemblies 18 have been inserted therein (forming the capsule body/pouch assemblies 144), to combine the two capsule sections 20a, 20b and complete the encapsulation process. See FIG. 12D which shows a capsule body/pouch assembly 144 in the opening 136 of wheel 106 after the insertion of the pouch assembly 18 into the capsule body 20a at the pouch processing section 164 as described in more detail below.

Figure 10:
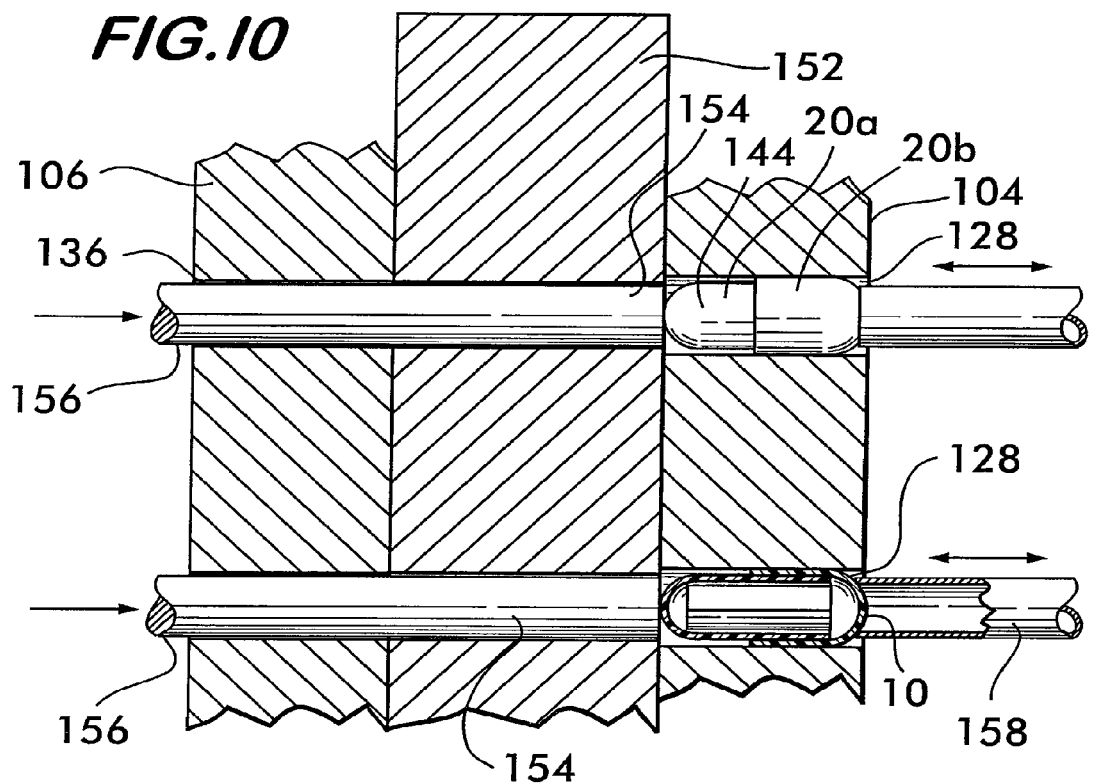
FIG. 10 is a view taken along line 10-10 of FIG. 4.

After receiving the body/pouch assemblies 144 at the pouch pressing section 164, the third wheel 106 indexes in the direction of arrow 140 (FIG. 4) and eventually reaches axial index position 150 where the two wheels 104, 106 overlap. With further reference to FIGS. 4 and 10, at the index position 150, the openings 128 of the second wheel 104 align with the openings 136 of the third wheel 106. The capsule body/pouch assemblies 144 are then transferred from the wheel 104 to a stationary spacer plate 152 having two transfer openings 154 sized for the capsule body/pouch assemblies 144. The spacer plate 152 takes up the gap between the wheels 106 and 104 and aligns the capsule body/pouch assemblies 144 for insertion into the caps 20b.

To effectuate the transfer and encapsulation process, a pair of cam operated push rods 156 having ends to match the curvature of the capsule bodies 20a advance to push the capsule body/pouch assemblies 144 from the wheel 106 through the openings 154 and into the openings 128 of wheel 104, and then dwell to prevent back sliding of the capsule body/pouch assemblies 144. A pair of cam operated capsule cap push rods 158 advance into the opening 128 of the wheel 104 to push the capsule caps 20b onto the capsule bodies 20a of the capsule body/pouch assemblies 144 a sufficient distance to lock the capsule sections 20a, 20b together as is known in the art, forming the encapsulated dosage forms 10. The push rods 156 thereafter push the dosage form 10 fully into the openings 128 of wheel 104. Both push rods 156, 158 then retract from respective openings 136, 128, to leave the dosage form 10 in the opening 128 of wheel 104.

Figure 11:
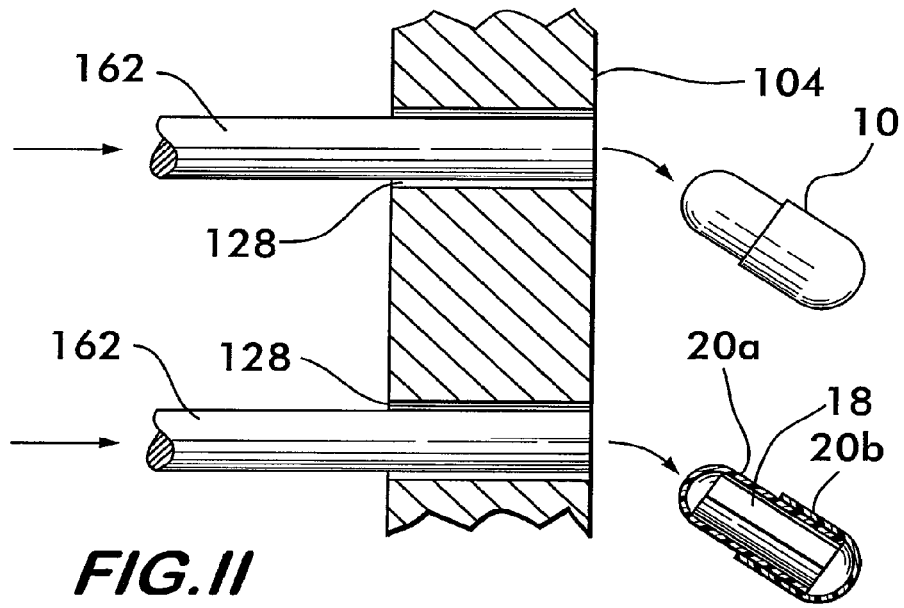
FIG. 11 is a view taken along line 11-11 of FIG. 4.

With further reference to FIG. 11, after completion of the encapsulation process at wheel axial position 150, the dosage forms 10, after several wheel 104 index movements in the direction of the arrow 132 (FIG. 4), arrives at the index position 160 where pusher rods 162 advance into the openings 128 to push out the dosage forms 10. The dosage forms 10 could be discharged onto an inspection holder where a vision system can inspect each dosage form 10. If acceptable, the dosage form 10 can be directed to one tray or bin, and if not acceptable, directed to another tray or bin in a manner known in the art.

Having described the various steps carried out by use of the wheels 102, 106, and 104, the steps of providing and wrapping the pouch assemblies 18 at pouch processing section 164 are now described in further detail. With reference to FIGS. 3, 3A, 4, and 5, and 5A, a pouch load subassembly 166 is provided for delivering pouch assemblies 18 to a pouch load tooling mechanism 168. As previously discussed, the pouch assemblies 18 are provided in the form of a continuous strip 32. Since the machine 100 processes two strips at a time, two strips 32 are provided as shown.

The pouch load subassembly 166 has a pouch strip servo-index system 170 (FIG. 3A) that has an outer gripper head 172 having two sections 172a, 172b, one for each strip 32, for engaging one side of the strips 32, and a single inner gripper head 174 for engaging the other side of both strips 32. In the present embodiment these gripper heads 172, 174 use vacuum to grip the strips 32 and thus are referred to herein as vacuum heads, although any suitable gripper head can be used.

The outer vacuum heads 172 are stationary and have vacuum ports configured preferably to hold the top portion of the strips 32 thereto. They also have channels 176 in which the ingredient section 12 of the pouch assembly can fit for slidable movement without damage (see also FIG. 12A). The inner vacuum head 174, having vacuum ports on both sides to hold the two strips 32 thereto, is positioned for indexed movement back and forth between first and second positions as shown by the arrow 178 in FIG. 3. The inner vacuum head 174 also has channels 176 in which the tablet section 12 of the pouch assembly can fit for slidable movement without damage.

For an index movement to the right as shown in FIG. 3, the vacuum in the inner vacuum head 174 is turned on to grip the top of the two strips 32 at a first position, and the vacuum in the outer vacuum heads 172 is turned off. The inner vacuum head 174 then indexes one pouch position to the right to a second position to deliver a pouch assembly 18 from each of the two strips 32 to a vacuum head 182 of the pouch load tooling mechanism 168 which has its own vacuum system for holding the pouch assemblies 18 as discussed below. A servo-motor (not shown) can provide the indexing motion to the inner vacuum head 174. A support member, not shown, can be provided to keep the strips 32 aligned and against the vacuum heads 172.

Figure 5A:
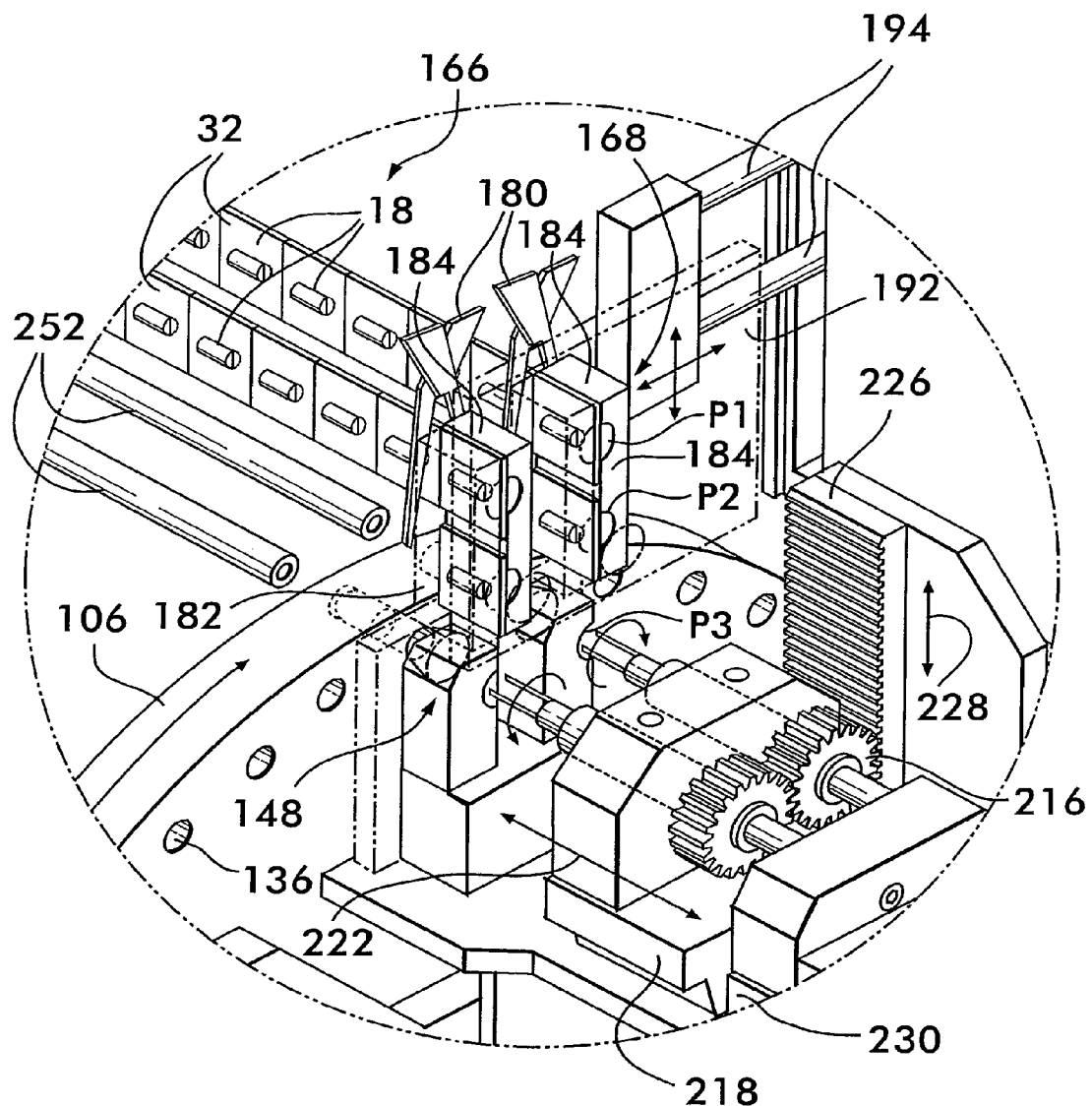
FIG. 5A is an enlarged view of the area shown in circle 5A of FIG. 5.

The delivered pouch assemblies 18, while held by vacuum to the pouch load tooling mechanism 168 (held by the vacuum heads 184 as seen in FIG. 5A), are then cut by pouch strip cutters 180, here formed as two scissors-type shearing mechanisms powered by pneumatic cylinders, although any suitable cutter may be used.

After the pouch assemblies 18 are cut from the strips 32, the vacuum in the inner vacuum head 174 is turned off to release the strips 32, and the vacuum in the outer vacuum heads 172 is turned on to grip the strips 32 (FIG. 3A). The inner vacuum head 174 then indexes back to its starting position (first position) to repeat the process of advancing the strips 32.

Figure 14:
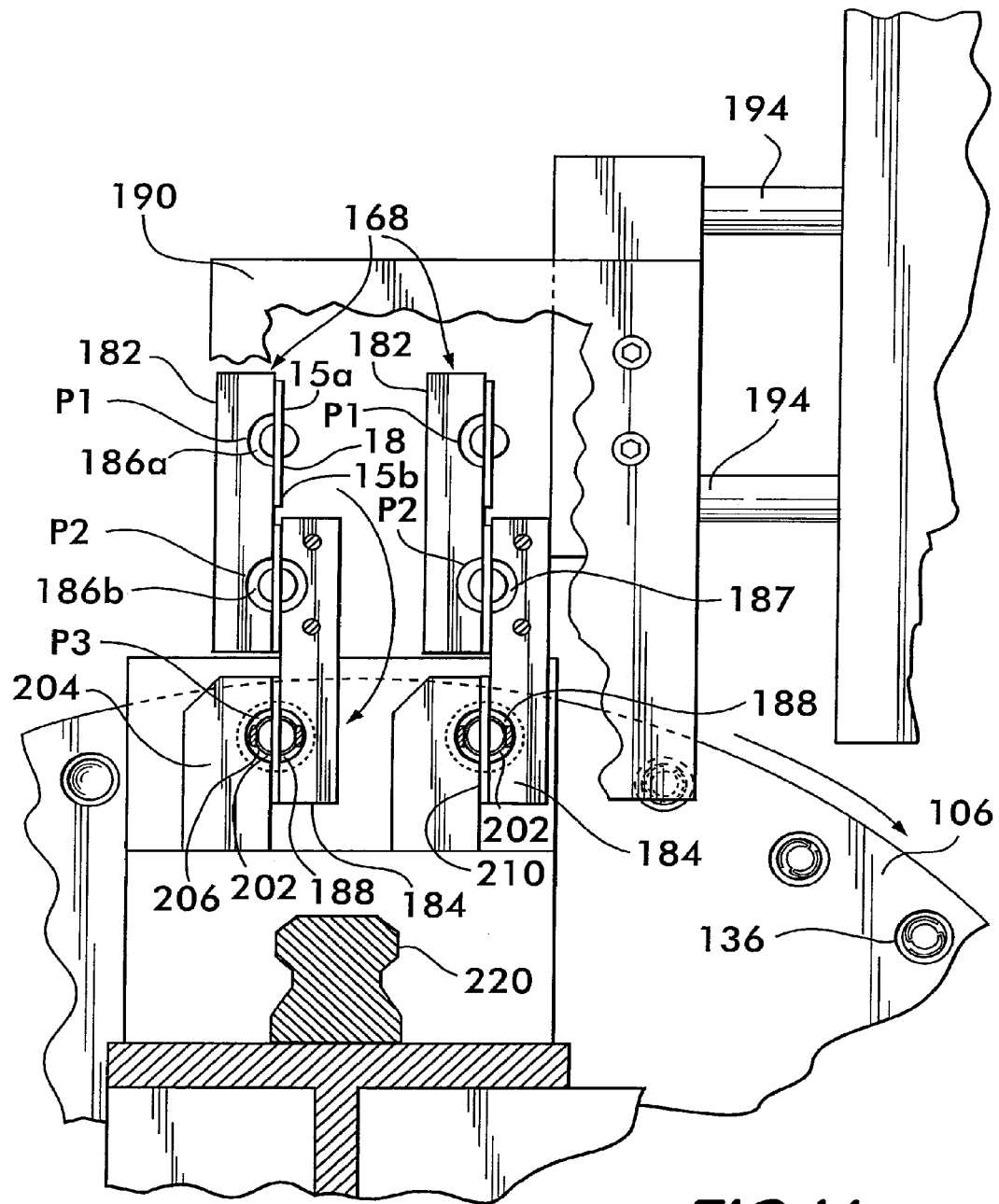
FIG. 14 is a view taken along line 14-14 of FIG. 9.

The pouch load tooling member 168 receives the individual pouch assemblies 18, grips them for the cutting process described above, and then transports them downward to the pouch wrapping subassembly 148 where the pouch assemblies 18 are wrapped. With reference to FIGS. 4, 5, 5A, 14, 15A, and 15B, the pouch load tooling mechanism 168 has two sets of a stationary gripper heads 182 (shown in dotted line in FIG. 5A) and vertical motion gripper heads 184 configured to compliment the stationary gripper heads 182, the left side set of stationary and motion gripper heads identified as reference numbers 182a and 184a respectively, and those on the right as 182b and 184b respectively. In the present embodiment these gripper heads 182, 184 use vacuum to grip the pouch assemblies 18 and thus are referred to herein as vacuum heads, although any suitable gripper head can be used. Each stationary vacuum head 182 has upper and lower pouch positions P1, P2 respectively defined by channels 186a, 186b configured to hold the ingredient section 12 without damaging it (FIG. 14). Each of the motion vacuum heads 184 have upper and lower channels 187, 188 respectively configured to hold the ingredient section 12 and to cooperate with the channels 186a, 186b of the stationary vacuum heads 182 for holding the pouch assemblies 18 in the channels. The two motion vacuum heads 184 are attached to a tie plate 190 by screws 192 (FIGS. 5, 5A in dotted lines) for uniform movement therewith in the direction shown by arrows 196 (FIG. 15A) via arms 194 connected to an x-y motion cam. A gap 198 between the stationary and motion vacuum heads 182, 184 is provided for the pouch assemblies 18 held between the two vacuum heads during the transport process (See also FIG. 13). As seen in FIGS. 15A and 15B, the motion vacuum heads 184 cycle between upper and lower positions as indicated by arrow 196 to move the pouch assemblies 18 downward in a series of steps from position P1, to position P2, and finally to position P3 at the pouch wrapping assembly 148.

When the motion vacuum heads 184 are in the lower position as illustrated in FIG. 15B, the pouch strips 32 are advanced by the pouch load subassembly 166 as described above to deliver additional pouch assemblies 18 to the upper position P1 of each of the stationary vacuum heads 182 (FIG. 5A), the vacuum to the vacuum ports in the vacuum heads 182 being off during the advancement of the strips 32. The vacuum is then turned on in the stationary vacuum heads 182 at P1 to hold the pouch assemblies 18 as they are cut from the strips 32 in the process previously described.

With continued reference to FIGS. 15A and 15B, the motion vacuum heads 184 then move to the upper position shown in dotted line in FIG. 15A, the vacuum in the stationary vacuum heads 182 is turned off, and a vacuum in the motion vacuum heads 184 is turned on to grab the pouch assemblies 18 at P1. The motion vacuum heads 184, holding the pouch assemblies 18, then move back to the lower position of FIG. 15B, moving the pouch assemblies from P1 to P2. The vacuums are again switched, vacuum in the motion vacuum heads 184 turned off to release the pouch assemblies and the vacuum in the stationary vacuum heads 182 turned on to grip the pouch assemblies 18 by the stationary vacuum heads 182. Then the motion vacuum heads 184 return without any pouch assemblies 18 to the upper position (FIG. 12A and the dotted lines in FIG. 15A) for another cycle of vacuum switches and movement of the motion vacuum heads 184 to move the pouch assemblies 18 from position P2 to the channel 206 (at P3) formed in the wrapping tool 204 of the pouch wrap subassembly 148. Thus it is seen that two cycles of movement of the motion vacuum heads 184 moves the pouch assemblies 18 from position P1 to P3, and that with each cycle, a new pouch assembly 18 is delivered to the wrapping channel 206 of the pouch wrapping subassembly 148, and new pouch assemblies are delivered to position P1 for cutting and to begin the transfer process.

In the pouch wrapping subassembly 148, the pouch flaps 15a, 15b are folded/wrapped after which the wrapped pouches are inserted into capsule bodies 20a by the pouch insert subassembly 200. As the pouch wrapping subassembly 148 and pouch insert subassembly 200 use similar elements, description of the two subassemblies is now described in further detail.

With reference to FIGS. 9, 14, 15A and 15B, the pouch wrapping subassembly 148 includes a pouch wrapping cavity 202 formed by the combination of the channels 206 of the wrapping tool 204 and the lower channels 188 of the motion vacuum heads 184 when the vacuum heads 184 are in the lower position. The tablet section 12 of the pouch assemblies 18 are held in the cavities 202 with the flaps 15a, 15b extending through cavity openings 208 into the gaps 210 between the motion vacuum heads 184 and the wrapping tool 204 as shown (FIG. 15B). The tie plate 190 has openings 195 (FIGS. 5, 9 and 12B) positioned to align with the wrapping cavities 202 when the vacuum heads 184 are in the lower position (FIG. 12B).

With further reference to FIGS. 5, 5A, 9 and 12A, the pouch wrapping subassembly 148 includes wrapping forks 212 connected by shafts through support block 214 to respective pinion gears 216 for rotation therewith, all mounted on a common slide carriage 218 which is movable on a stationary rail 220 in the direction of arrow 222 (FIG. 5A). Each of the wrapping forks 212 have two tines 224 configured to move into the respective wrapping cavity 202, upon movement of the carriage 218, between the pouch assembly 18 and the wall 203 of the cavity 202 to rotate the pouch assembly 18 and thereby wrap the flaps 15a, 15b as the flaps are pulled into the cavity 202 through the slots 210 (FIGS. 15A and 15B). To rotate the forks 212, one of the pinion gears 216 engages the second pinion gear on one side, and engages a cam driven vertical rack 226 on the other side which moves downward (arrow 228 in FIG. 5A) to provide the rotary motion.

Figure 9:
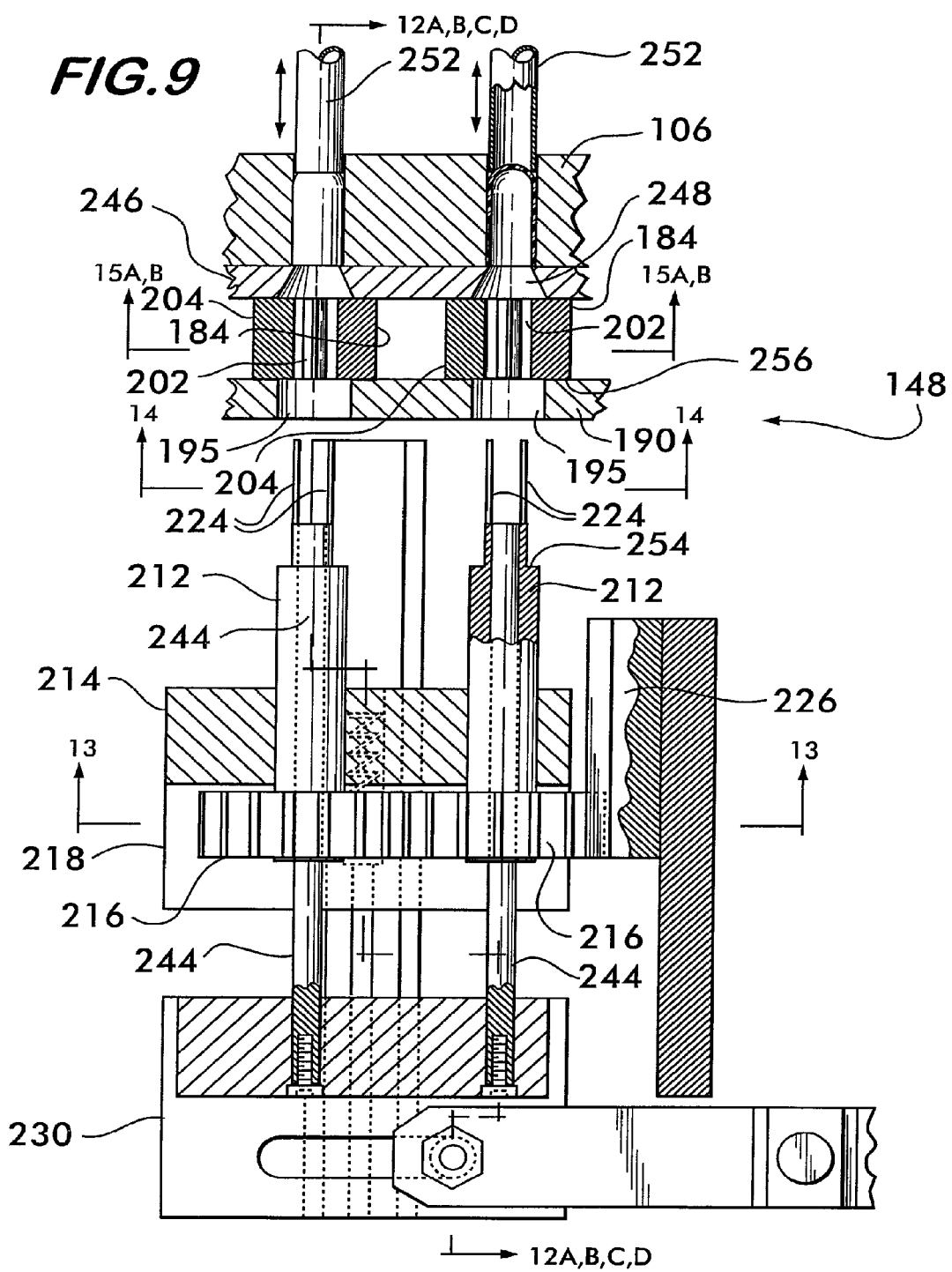
FIG. 9 is a view taken along line 9-9 of FIG. 5.
Figure 12A:
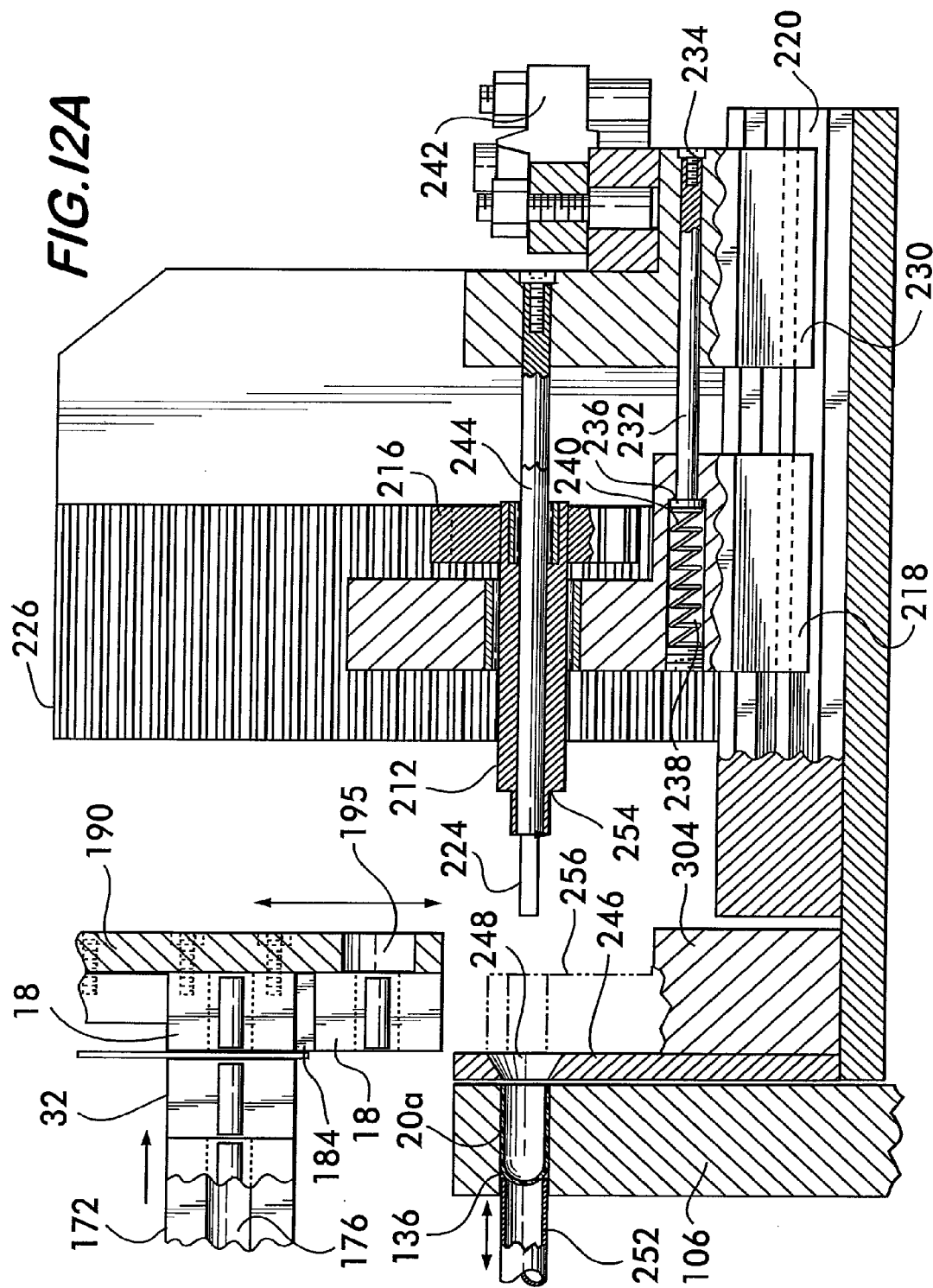
FIG. 12A is a cross sectional view taken along line 12-12 of FIG. 9 showing the wrapping fork in the fully withdrawn position.

With further reference to FIGS. 5, 9 and 12A, a second carriage 230 spaced from the first carriage 218 is likewise movable on the stationary rail 220 in the direction of arrow 222 (FIGS. 5, 5A). The two carriages 218 and 230 are attached together by tie rod 232 fixedly attached at one end 234 to the carriage 230 and having a shoulder 236 at its other end moveable within a cavity 238 within the carriage 218 (FIG. 12A). A spring 240 maintains the shoulder 236 at the far right end of the cavity 238 as seen in FIG. 12A so that the two carriages 218 and 230 will move in unison together motivated by a cam actuator 242 attached to carriage 230 until, when moving to the left in FIG. 12A, the forward progress of carriage 218 is stopped and the force of spring 240 is overcome, allowing the carriage 230 to continue moving to the left as described below.

Figure 12B:
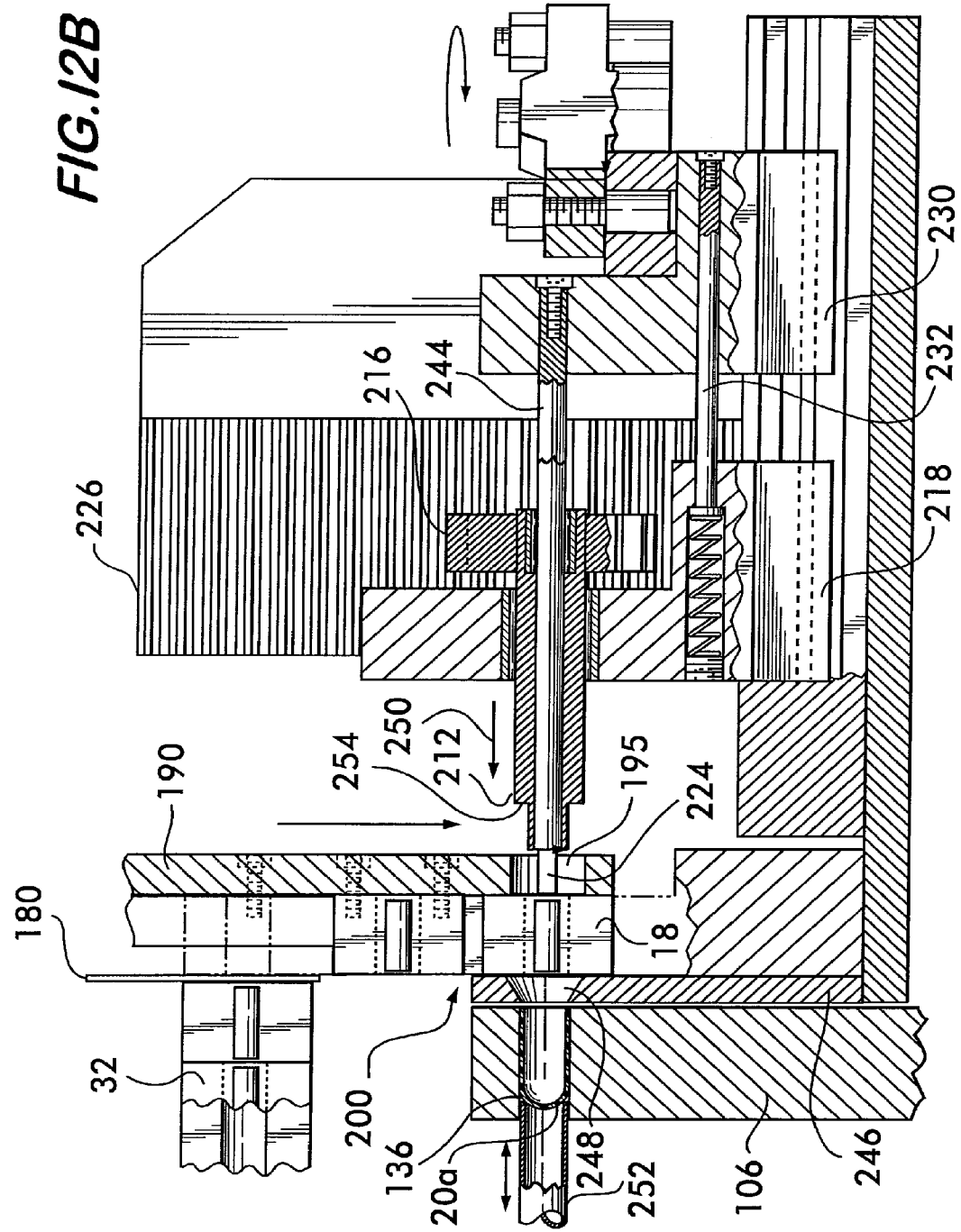
FIG. 12B is a cross sectional view taken along line 12-12 of FIG. 9 showing the wrapping fork entering the wrapping cavity after forward movement of the wrapping fork.
Figure 12D:
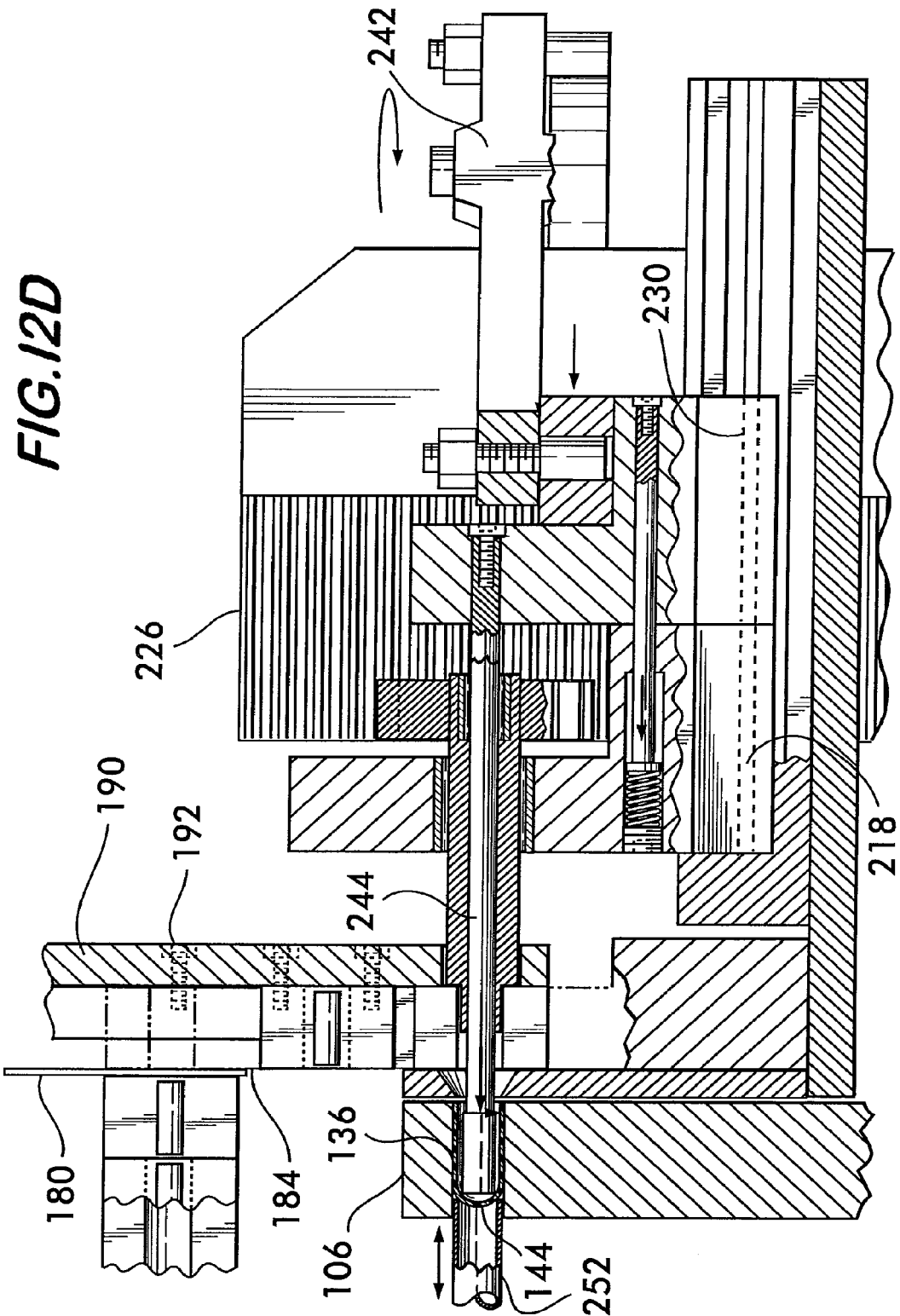
FIG. 12D is a cross sectional view taken along line 12-12 of FIG. 9 showing the pouch assembly fully inserted into the capsule body by the push rod.
Figure 13:
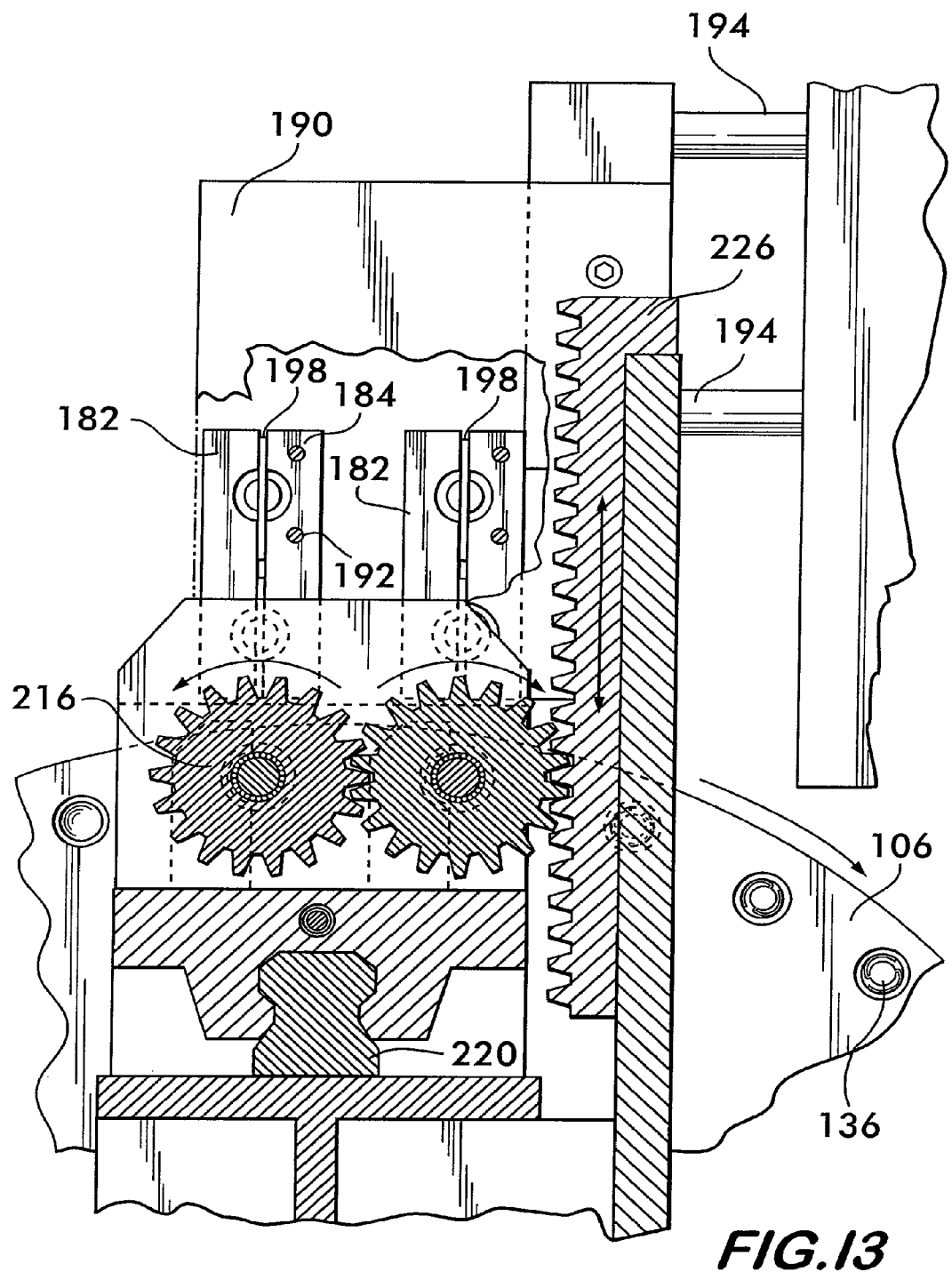
FIG. 13 is a view taken along line 13-13 of FIG. 9.

Thus, with reference to FIGS. 5, 9, 12A, and 12B after the pouch assemblies 18 are transferred to the pouch wrapping cavities 202, formed by the combination of the wrapping tool 204 and the motion vacuum heads 184, and the vacuum to the motion vacuum heads 184 is turned off, the cam actuator 242 moves the carriages 230 and 218 to the left as shown in FIGS. 12A, 12B, moving the forks 212 through the tie plate openings 195 and into the wrapping cavity 202 as shown in FIGS. 15A, 15B. Once the tines 224 engage the pouch assembly 18, the rack 226 is moved downward by a cam drive to rotate the forks 212 and thereby wrap the pouch assembly flaps 15a, 15b.

Once the flaps are wrapped, a pouch insert subassembly 200 inserts the wrapped pouch into a capsule body 20a. With reference to FIGS. 5A, 9, 12A, 12C and 12D, the pouch insert subassembly 200 includes the carriage 230, pouch push rods 244 fixedly attached to the carriage 230 and extending longitudinally within the wrapping forks 212 (on carriage 218), and funnel plates 246 having two funnel shaped openings 248 positioned between and aligned with the wrapping cavities 202 and openings 136 in the wheel 106. The funnel shaped openings 248 have a one end adjacent to the wheel openings 136 which are preferably sized slightly smaller than the width/diameter of the wheel opening 136. As the wrapping process is completed, the forward movement of carriage 218 (arrow 250 in FIG. 12B) and rotation of the forks 212 is stopped while the carriage 230 continues moving forward via the cam drive 242. It is seen that continued forward movement of the carriage 230, which compresses the spring 240, advances the push rods 244 between the tines 224 to push the wrapped pouch assemblies 18 through the funnel opening 248 into the capsule bodies 20a in the wheel openings 136. Cam driven back-up rods 252 engage the back side of the capsule bodies 20a to prevent the capsule bodies 20a from moving from the position shown whereby the capsule's open end is flush with the inner face of the wheel 106 as shown (FIG. 12B) during the insertion process. The forward movement of the carriage 218 can be stopped in numerous ways, including the use of a shoulder 254 on the forks 212 which engages the outer wall 256 of the wrapping cavities 202 (FIG. 12A). After the insertion process is complete, the cam actuator 242 reverses the direction of the carriage 230, moving both it and the carriage 218 as the spring 240 uncompresses back to their starting position shown in FIG. 12A. These steps repeat for the next pair of pouch assemblies.

With the pouch assemblies 18 inserted into the capsule bodies 20a, the wheel 106 indexes forward in the direction of arrow 140 (FIG. 4), and the insertion process begins with the capsule bodies 20a in the adjacent set of wheel openings 136. At the index position 150, when the openings 136 in wheel 106 align with the openings 128 in the wheel 104, the capsule body/pouch assemblies 144 are combined with capsule caps 20b as previously described, although not necessarily with the same caps 20b that were separated from the particular capsule bodies 20a.

Having described the arrangements of the various elements of the machine 100, the sequence of steps carried out by the machine 100 is now described with reference to FIGS. 3, 4, and 5, and any of the more detail drawings previously described as may be helpful. First, it is seen that capsules 20 are provided in the capsule feeder 110, and two strips 32 of pouch assemblies 18 are provided to the machine 100 by loading the strips into the pouch strip indexing system 170.

The capsule feed tubes 112 are filled with capsules 20 oriented such that the capsule bodies 20a enter the wheel 102 openings 114 first at wheel index position 116. After the capsules 20 are inserted into the openings 114 and separated therein into capsule bodies 20a and capsule caps 20b, the wheel 102 is indexed in the direction of arrow 126 (FIG. 4). At wheel index position 130, the capsule caps 20b are transferred from the first wheel 102 to openings 128 in the second wheel 104. At wheel index position 138, the capsule bodies 20a are transferred from the first wheel 102 to openings 136 in the third wheel 106. It is understood that with each index movement of the wheels 102, 104, and 106, the above transfers and processes take place for different sets of capsules 20, and that other capsule sections are transferred between the various index positions for further processing. In the present embodiment, each wheel 102, 104, 106 moves or rotates two openings 114, 128, 136 with each index movement.

With each index movement of the wheels, the pouch assemblies 18 are fed into the machine 100 via the pouch load subassembly 166 which uses the pouch servo-index system 170 to move the pouch assemblies. The pouch assemblies 18 are cut from the strips 32 by cutters 180 and transferred downward by the pouch load tooling mechanism 168 to the wrapping cavities 202 of the pouch wrapping subassembly 148.

Once the pouch assemblies 18 are positioned in the wrapping cavities 202, the wrapping forks 212 advance into the wrapping cavities 202 and rotate to wrap the pouch assemblies 18. Push rods 244 then advance to push the wrapped pouches through the funnel plate 246 into capsule bodies 20a held in openings 136 of the third wheel 106 by push rods 252 to prevent movement of the capsule body during the insertion process.

When the capsule body/pouches 144 in wheel 106 move to the wheel index position 150, the capsule body/pouches 144 are transferred from wheel 106 to openings 128 in wheel 104 through the spacer plate 152 to the wheel 106 and combined with capsule caps 20b to complete the encapsulation process. The wheel 106 then indexes to index position 160 where the completed gastro-retentive devices 10 are pushed out of the openings (FIG. 11).

It is seen that the various steps described above take place simultaneously after each indexing of the wheels, the process being repeated in a continuous manner for each set of pouch assemblies 18 and capsules 20. For example, after an index movement of the wheels 102, 104, 106, a new set of capsules 20 are loaded into the wheel 102 and separated into capsule bodies 20a and caps 20b, a set of capsule caps 20b is transferred from wheel 102 to wheel 104 at index position 130, a set of cap bodies 20a is transferred from wheel 102 to wheel 106 at index position 138, pouch assemblies are transferred to the stationary vacuum head 182 and cut from strip 30, pouch assemblies 18 are loaded into cap bodies 20a in wheel 106 at insert subassembly 200, capsule bodies 20a containing pouch assemblies 18 are combined with capsule caps 20b and transferred from wheel 106 to wheel 104 at index position 150, and encapsulated pouches (gastro-retentive device 10) are off loaded at index position 160. The wheels then index and the process begins again.

Various control systems can be used to control the operation of the machine 100 as is known in the art. For example, with reference to FIG. 16, a master machine controller can be provided for the principal operator interface and also control the encapsulating machine I/O, servo motion and data reporting. Additionally, a vision testing system can be used for inspecting faults during the manufacturing process. For example, a vision inspection system could be used to detect and reject if necessary faulty pouch assemblies 18 before insertion into a capsule body, and to inspect the finished gastro-retentive device 10 and reject defective dosage forms 10.

Any suitable materials as known in the art may be sued for the various components. For example, ANSI 316 Stainless Steel may be used for product contact surfaces. These surfaces and associated welds should be polished to a number 7 mirror finish. ANSI 304 Stainless Steel may be used elsewhere. A number 4 finish can be provided for naked (non-shed) metallic non-product contact surfaces and welds.

The present invention as described above provides an economical means of producing an advantageous gastro-retentive form 10. It is understood that the above described embodiment is a preferred embodiment of the invention, and that it is not intended to limit the invention to such disclosure. Changes and modifications may be incorporated and embodied within the scope of the invention.

What is claimed is:

1. A process of separating and combining capsule sections; comprising:
   (A) delivering a capsule to an opening in a first rotatable wheel having multiple openings;
   (B) rotating said first wheel so that said opening aligns with an opening in a second rotatable wheel which has multiple openings;
   (C) separating said first and second capsule sections and moving said second capsule section to said opening in said second wheel;
   (D) rotating said first wheel so that said opening in said first wheel aligns with an opening in a third rotatable wheel which has multiple openings, and then moving said first capsule section from said opening in said first wheel to said opening in said third wheel; and
   (E) rotating said third wheel so that said opening in said third wheel aligns with one of said openings in said second wheel, and then combining said first capsule section with a second capsule section which may include said second capsule section or another second capsule section.

2. An apparatus for the manufacture of a gastro-retentive device comprising a capsule surrounding a pouch assembly, said capsule having first and second capsule sections and said pouch assembly having at least one flap;
   said apparatus comprising:
   a first rotatable wheel having an opening for receiving said capsule;
   a second rotatable wheel having an opening for receiving said second capsule section, said second wheel being positionable relative to said first wheel such that said opening of said first wheel aligns with said opening of said second wheel at an axial position of said first and second wheels so as to be capable of transferring said second capsule section from said first wheel to said second wheel;
   a third rotatable wheel having an opening for receiving said first capsule section, said third wheel being positionable relative to said first wheel such that said opening of said first wheel aligns with said opening of said third wheel at an axial position of said first and third wheels so as to be capable of transferring said first capsule section from said first wheel to said third wheel;
   a pouch wrapping subassembly having a cavity in which said pouch assembly can be wrapped, said subassembly including a fork insertable into said cavity for wrapping said flap around an ingredient section of said pouch assembly; and
   a pouch insert subassembly for inserting said wrapped pouch assembly into said first capsule section, said third wheel having an axial position in which said opening of said third wheel aligns with said cavity for receiving said wrapped pouch assembly into said first capsule section within said opening.

3. An apparatus in accordance with claim 2 wherein said third wheel is positionable relative to said second wheel such that said opening of said second wheel aligns with said opening of said third wheel at an axial position of said third and second wheels so that said first capsule section with said pouch assembly can be combined with said second or other second capsule section.

4. The apparatus of claim 2 wherein two openings of said first wheel simultaneously align with two openings of said second wheel at said axial position of said first and second wheels.

5. An apparatus for use in the manufacture of a device having a capsule which is formed of a first capsule section and a second capsule section, said device comprising:
   a first rotatable wheel having a plurality of openings configured for receiving said capsule;
   a second rotatable wheel having a plurality of openings configured for receiving said second capsule section of said capsule from said first wheel, said second wheel being positioned relative to said first wheel such that at least one of said openings of said first wheel aligns with at least one of said openings of said second wheel at an axial position of the said first and second wheels so as to be capable of transferring said second capsule section from said first wheel to said second wheel;
   a third rotatable wheel having a plurality of openings configured for receiving said first capsule section from said first wheel, said third wheel being positioned relative to said first wheel such that at least one of said openings of said first wheel aligns with at least one of said openings of said third wheel at an axial position of said first and third wheels so as to be capable of transferring said first capsule section from said first wheel to said third wheel; and
   said third wheel further being positioned relative to said second wheel such that at least one of said openings of said second wheel aligns with at least one of said openings of said third wheel at an axial position of said third and second wheels.

6. The device on accordance with claim 5 wherein said first wheel is adjacent to said second and said third wheels, and said third wheel is separated from said second wheel by a spacer having an opening aligning with said at least one openings of said third and second wheels at said axial position, said spacer opening being sized to allow at least one of said first and second capsule sections to pass there through.

* * * * *